(12) United States Patent
Wood et al.

(10) Patent No.: US 7,009,043 B1
(45) Date of Patent: Mar. 7, 2006

(54) PLUS END-DIRECTED MICROTUBULE MOTOR REQUIRED FOR CHROMOSOME CONGRESSION

(75) Inventors: Kenneth W. Wood, Foster City, CA (US); Roman Sakowicz, Foster City, CA (US); Lawrence S. B. Goldstein, San Diego, CA (US); Don W. Cleveland, Delmar, CA (US)

(73) Assignee: The Regents of the University of California, Oakland, CA (US)

( * ) Notice: Subject to any disclaimer, the term of this patent is extended or adjusted under 35 U.S.C. 154(b) by 767 days.

(21) Appl. No.: 09/724,584

(22) Filed: Nov. 28, 2000

Related U.S. Application Data

(63) Continuation of application No. 09/150,867, filed on Sep. 10, 1998.
(60) Provisional application No. 60/058,645, filed on Sep. 11, 1997.

(51) Int. Cl.
*C07H 21/04* (2006.01)
*C12N 15/11* (2006.01)
*C12N 15/85* (2006.01)
*C12N 15/63* (2006.01)

(52) U.S. Cl. .................... 536/23.5; 536/23.1; 435/69.1; 435/70.1; 435/70.3; 435/71.1; 435/320.1; 435/325

(58) Field of Classification Search ................. 435/69.1, 435/70.1, 70.3, 71.1, 320.1, 325; 536/23.5, 536/23.1
See application file for complete search history.

(56) References Cited

PUBLICATIONS

Bowie et al (Science, 247: 1306–1310, 1990).*
Burgess et al (J. Cell Biology, 111: 2129–2138, 1990).*
Lazar et al (Molecular and Cellular Biology, 8: 1247–1252, 1988).*
Brown et al., "Cyclin–like accumulation and loss of the putative kinetochore motor CENP–E results from coupling continuous synthesis with specific degradation at the end of mitosis," *J Cell Biol* 125:1303–12 [1994].
Duesbery et al., "CENP–E is an essential kinetochore motor in maturing oocytes and is masked during mos–dependent, cell cycle arrest at metaphase II," *Proc Natl Acad Sci U S A* 94:9165–7 [1997].
Hyman and Mitchison, "Two different microtubule–based motor activities with opposite polarities in kinetochores," *Nature* 351:206–11 [1991].
Kodama et al., "The initial phosphate burst in ATP hydrolysis by myosin and subfragment–1 as studied by a modified malachite green method for determination of inorganic phosphate," *J Biochem* (*Tokyo*) 99:1465–72 [1986].
Liao et al., "Mitotic regulation of microtubule cross–linking activity of CENP–E kinetochore protein," *Science* 265:394–8 [1994].
Lombillo et al., "Antibodies to the kinesin motor domain and CENP–E inhibit microtubule depolymerization–dependent motion of chromosomes in vitro," *J. Cell Biol* 128:107–15 [1995].
Mitchison and Kirschner, "Properties of the kinetochore in vitro. II. Microtubule capture and ATP–dependent translocation," *J Cell Biol* 101:766–77 [1985].
Rattner et al., "The centromere kinesin–like protein, CENP–E. An autoantigen in systemic sclerosis," *Arthritis Rheum* 39:1355–61 [1996].
Sakowicz et al., "A marine natural product inhibitor of kinesin motors," *Science* 280:292–5 [1998].
Stewart et al., "Direction of microtubule movement in an intrinsic property of the motor domains of kinesin heavy chain and Drosphila ncd protein," *Proc Natl Acad Sci U S A* 90:5209–13 [1993].
Thrower et al., "Mitotic HeLa cells contain a CENP–E–associated minus end–directed microtubule motor," *EMBO J* 14:918–26 [1995].
Wood et al., "CENP–E is a plus end–directed kinetochore motor required for metaphase chromosome alignment," *Cell* 91:357–66 [1997].
Yen et al., "CENP–E, a novel human centromere–associated protein required for progression from metaphase to anaphase," *EMBO J* 10:1245–54 [1991].
Yen et al., "CENP–E is a putative kinetochore motor that accumulates just before mitosis," *Nature* 359:536–9 [1992].
Gordon et al., "Overexpression of the kinetochore localization domain of CENP–E causes two distinct dominant negative phenotypes," *Mol Biol Cell* 7 Supplement:565a [1996].
Wood et al., "Characterization of a Xenopus homologue of centromere–associated protein–E (CENP–E)," *Mol Biol Cell* 6 Supplement:361a [1995].
Vafa, O. et al. Mol. Biol. of the Cell, 8 (suppl): 125A, 1997, Nov.*

* cited by examiner

*Primary Examiner*—Anthony C. Caputa
*Assistant Examiner*—Anne L. Holleran
(74) *Attorney, Agent, or Firm*—Medlen & Carroll, LLP

(57) ABSTRACT

The invention provides isolated nucleic acid and amino acid sequences of Xenopus CENP-E (XCENP-E), antibodies to XCENP-E, methods of screening for CENP-E modulators using biologically active CENP-E, and kits for screening for CENP-E modulators.

13 Claims, 4 Drawing Sheets

```
MSEGDAVKVCVRVRPLIQREQGDQANLQWKAGNNTISQVDGIKSFNFDRV    50
FNSHESTSQIYQEIAVPTTRSALQGYNGTIFAYGQTSSGKTYTMMGTPNS   100
LGIIPQAIQEVEKIIQEIENREFLLRVSYMEIYNETVKDLLCDDRRKKPL   150
EIREDFNRNVYVADLTEEIMMVPEHVIQWIKKGEKNRHYGETKHNDHSSR   200
SHTIFRMIVESRDRNDETNSENCDGAMMVSHLNLVDLAGSERASQTGAEG   250
VRLKEGCNINRSLFILGQVIKKLSDGQAGGFINYRDSKLTRILQNSLGGN   300
AKTVIICTITPVSRDETISTLQFASTAKHVRNTBHVNEVLDDEALLKRYR   350
KEILDLKKQLENLESSSETKAQAMAKEEHTQLIAEIKQLHKEREDRIWHL   400
INIVMASSQESQQDQRVKRKRRVTWAPGKIQNSLHASGVSDFDMLSRIPG   450
NFSKKAKFSDMPSFPEIDDSVCTEFSDFDDALSMMDSNGIDAEWNLASKV   500
THREKTSLHQSMIDFGQISDSVQFHDSSKENQLQYLPKDSGDMAECRKAS   550
FEKEITSLQQQLQSKEEEKKELVQSFELKIAELEEQLSVKAKNLEMVTNS   600
REHSINAEVQTDVEKEVVRKEMSVLGDSGYNASNSDLQDSSVDGKRLSSS   650
HDECIEHRKMLEQKIVDLEEFIENLNKKSENDKQKSSEQDFMESIQLCEA   700
IMAEKANALEEIALMRONFDNIILENETLKREIADLERSLKENQETNEFE   750
ILEKETQKEHEAQLIHEIGSLKKLVENAEMYNQNLDEDLETKTKLIKEQE   800
IQLAEIRKRADNLQKKVRNFDLSVSMGDSEKLCEEIFQLKQSLSDAEAVT   850
RDAQKECSFLRSENLELKEKMEDTSNWYNQKEKAASIFEKQLETEKSNYK   900
KMEADIQKELQSAFNEINYINGILAGKVPRDLLSRVELEKKVSEFSKQLE   950
KALEEKNAIENEVTCLSEYKFLPNEVEQLKNQISKASEEIMLLKQEGEHS  1000
ASIISKQEIIMQEQSEQILQLTDEVTHTQSKVQQTEEQYLEMKKMHDDLF  1050
EKYIRNKSEAEDILREMENLKGTMESVEVKIADTKHELEETIRDKEQLLH  1100
EKKYFFQAMQTIFPITPISDSLPPSKLVEGNSQDPIEINDYHNLIALATE  1150
RNNIMVCLETERNSLREQVIDINTQLQSLQAQSIEKSDLQKPKQDLEEGE  1200
VKLLLEMELLKGHLTDSQLSIEKLQLENLEVTEKIQTIQEEMKNITIERN  1250
ELQTNFEDLKAEHDSLKQDISENIEQSIETQDELRAAQEEIREQKQLVDS  1300
FRQQLLDCSVGISSPNHDAMANQEKVSLGEVNSLQSEMLRGERDELQTSC  1350
KALVSELELLRAHVKSVEGENLEITKKINGIEKEILGKSEESEVLKSMLE  1400
NLKEDNNKLKEQAEEYSSKENQFSLEEVFSGSQKLVDEIEVLKAQLKAAE  1450
ERLEIKDRDYFELVQTANTNLVEGKDETPLQADHEEDSIDRRSEEMEIKV  1500
```

*FIG. 1C1.*

```
LGEKLERNQYLDERLQEEKLELSNKLEILQKEMETSVLLKDDLQQKLESL  1550
LSENIILKENIDTTLKHHSDTQAQLQKTQQELQLAKNLAIAASDNCPITQ  1600
EKETSADCVHPLEEKIDLLTEEHQKTNEQEKLLHEKNELEQAQVELKCE   1650
VEHIMKSMIESKSSLESLQHEKHDTEQQLLALKQQMQVVTQEKKELQQTH  1700
EHLTAEVDHLKENIELGLNFKNEAQQKTTKEQCLLNENKELEQSQHRLQC  1750
EIEELMKSLKDKESAIETLKESEQKVINLNQEMEMVMLEMEELKNSQRTV  1800
IAERDQLQDDLRESMEMSIETQDDLRKAQEALQQKDKVQELTSQISVLQ   1850
EKISLLENQMLYNVATVKETLSERDDLNQSKQHLFSEIETCSLSLKEKEF  1900
ALEQAERDKADAARKTIDITEKISNLEEQLLQQATHLKETQYERESLIQC  1950
KEQLALNTEHLRETLKSKDLALGKMEQERDEAANKVIALTEKMSSLEEQI  2000
NENVTTLKEGEGEKETFYLQRPSKQQSSSQMEELRESLKTKDLQLEEAEK  2050
EISEATNEIKNLTAKISSLEEEILQNASILNEAVSERENLRHSKQQLVSE  2100
LEQLSLTLKSRDHAFAQSKREKDEAVNKIASLAEEIKILTKEMDEFRDSK  2150
ESLQEQSSHLSEELCTYKTELQMLKQQKEDINNKLAEKVKEVDELLQHLS  2200
SLKEQLDQIQMELRNEKLRNYELCEKMDIMEKEISVLRLMQNEPQQEFDD  2250
VAERMDILESRNQEIQELMEKISAVYSEQHTLLSSISSELQKETEAHKHC  2300
MLNIKESLSSTLSRSFGSLQTEHVKQNTQLQTLLNKFKMVYRTAAVKEDH  2350
SLTKDYEKDLAAEQKRHDELRLQLQCLEQHGRKWSDSASEEDKFCEIEFL  2400
NELLFKKANITQSVQDDFSEVQVFLNQVGSTLQEELEHKKGFMQWLEEFG  2450
DLHVLAKKISEGMQENRRIASTIQLLTKRLKAVVQSKIQREITVYLNQF   2500
EAKLQEKKEQNKELMRRMEHHGPSASVMEEENARLLGILKTVQDESKKLQ  2550
SRIKMLENELNLVKDDAMHKGEKVAILQDKLLSRNAEAELNAMQVKLTKK  2600
QDNLQAAMKELENLQKMVAKGAVPYKEEIDNLKIKVVKIEMEKIKYSKAT  2650
DQEIAYLKSCLEDKEEGLRRIKDELRRAQADNDITVCVPKDYQKASTFEV  2700
TCGGGSGIVQSTAMLVLQSEKAALEREHLSHYKKKYHHLSRTMSSSEDRKK  2750
TKAKSDAHSSHTGSSHRGSPHKIETYRHGPVIPERSEMRSLHLGSPKKSE  2800
SSTKRVVSPNRSEIYSQLVMSPGKTGHHKHILSPSKVGLHKKRALSPNRS  2850
EMPTQHVISPGKTGLHKNILESTIEDNLSSPCKQQKVQENLNSPKGKLED  2900
VKSKSMEYCPSQFFDNSKLGDFSELNTAESNDKSQAENWWYEAKKETAPE  2950
CKTS
```

*FIG. 1C2.*

SEQUENCE LISTING

```
<160> NUMBER OF SEQ ID NOS: 11

<210> SEQ ID NO 1
<211> LENGTH: 2954
<212> TYPE: PRT
<213> ORGANISM: Xenopus sp.
<220> FEATURE:
<223> OTHER INFORMATION: Xenopus centromere-associated protein-E
      (XCENP-E) member of the kinesin superfamily of microtubule motor
      proteins
<220> FEATURE:
<221> NAME/KEY: DOMAIN
<222> LOCATION: (1)..(472)
<223> OTHER INFORMATION: kinesin like motor domain
<220> FEATURE:
<221> NAME/KEY: DOMAIN
<222> LOCATION: (473)..(2752)
<223> OTHER INFORMATION: rod domain
<220> FEATURE:
<221> NAME/KEY: DOMAIN
<222> LOCATION: (2753)..(2954)
<223> OTHER INFORMATION: tail domain

<400> SEQUENCE: 1

Met Ser Glu Gly Asp Ala Val Lys Val Cys Val Arg Val Arg Pro Leu
 1               5                  10                  15

Ile Gln Arg Glu Gln Gly Asp Gln Ala Asn Leu Gln Trp Lys Ala Gly
            20                  25                  30
```

```
-continued

Asn Asn Thr Ile Ser Gln Val Asp Gly Thr Lys Ser Phe Asn Phe Asp
        35                  40                  45

Arg Val Phe Asn Ser His Glu Ser Thr Ser Gln Ile Tyr Gln Glu Ile
        50                  55                  60

Ala Val Pro Ile Ile Arg Ser Ala Leu Gln Gly Tyr Asn Gly Thr Ile
 65                  70                  75                  80

Phe Ala Tyr Gly Gln Thr Ser Ser Gly Lys Thr Tyr Thr Met Met Gly
                85                  90                  95

Thr Pro Asn Ser Leu Gly Ile Ile Pro Gln Ala Ile Gln Glu Val Phe
                100                 105                 110

Lys Ile Ile Gln Glu Ile Pro Asn Arg Glu Phe Leu Leu Arg Val Ser
            115                 120                 125

Tyr Met Glu Ile Tyr Asn Glu Thr Val Lys Asp Leu Leu Cys Asp Asp
        130                 135                 140

Arg Arg Lys Lys Pro Leu Glu Ile Arg Glu Asp Phe Asn Arg Asn Val
145                 150                 155                 160

Tyr Val Ala Asp Leu Thr Glu Glu Leu Val Met Val Pro Glu His Val
                165                 170                 175

Ile Gln Trp Ile Lys Lys Gly Glu Lys Asn Arg His Tyr Gly Glu Thr
            180                 185                 190

Lys Met Asn Asp His Ser Ser Arg Ser His Thr Ile Phe Arg Met Ile
        195                 200                 205

Val Glu Ser Arg Asp Arg Asn Asp Pro Thr Asn Ser Glu Asn Cys Asp
        210                 215                 220

Gly Ala Val Met Val Ser His Leu Asn Leu Val Asp Leu Ala Gly Ser
225                 230                 235                 240

Glu Arg Ala Ser Gln Thr Gly Ala Glu Gly Val Arg Leu Lys Glu Gly
                245                 250                 255

Cys Asn Ile Asn Arg Ser Leu Phe Ile Leu Gly Gln Val Ile Lys Lys
            260                 265                 270

Leu Ser Asp Gly Gln Ala Gly Gly Phe Ile Asn Tyr Arg Asp Ser Lys
        275                 280                 285

Leu Thr Arg Ile Leu Gln Asn Ser Leu Gly Gly Asn Ala Lys Thr Val
        290                 295                 300

Ile Ile Cys Thr Ile Thr Pro Val Ser Phe Asp Glu Thr Leu Ser Thr
305                 310                 315                 320

Leu Gln Phe Ala Ser Thr Ala Lys His Val Arg Asn Thr Pro His Val
                325                 330                 335

Asn Glu Val Leu Asp Asp Glu Ala Leu Leu Lys Arg Tyr Arg Lys Glu
            340                 345                 350

Ile Leu Asp Leu Lys Lys Gln Leu Glu Asn Leu Glu Ser Ser Ser Glu
        355                 360                 365

Thr Lys Ala Gln Ala Met Ala Lys Glu Glu His Thr Gln Leu Leu Ala
        370                 375                 380

Glu Ile Lys Gln Leu His Lys Glu Arg Glu Asp Arg Ile Trp His Leu
385                 390                 395                 400

Thr Asn Ile Val Val Ala Ser Ser Gln Glu Ser Gln Gln Asp Gln Arg
                405                 410                 415

Val Lys Arg Lys Arg Arg Val Thr Trp Ala Pro Gly Lys Ile Gln Asn
            420                 425                 430

Ser Leu His Ala Ser Gly Val Ser Asp Phe Asp Met Leu Ser Arg Leu
        435                 440                 445

Pro Gly Asn Phe Ser Lys Lys Ala Lys Phe Ser Asp Met Pro Ser Phe
```

```
            450              455              460
Pro Glu Ile Asp Asp Ser Val Cys Thr Glu Phe Ser Asp Phe Asp Asp
465                 470                 475                 480

Ala Leu Ser Met Met Asp Ser Asn Gly Ile Asp Ala Glu Trp Asn Leu
                485                 490                 495

Ala Ser Lys Val Thr His Arg Glu Lys Thr Ser Leu His Gln Ser Met
                500                 505                 510

Ile Asp Phe Gly Gln Ile Ser Asp Ser Val Gln Phe His Asp Ser Ser
                515                 520                 525

Lys Glu Asn Gln Leu Gln Tyr Leu Pro Lys Asp Ser Gly Asp Met Ala
530                 535                 540

Glu Cys Arg Lys Ala Ser Phe Glu Lys Glu Ile Thr Ser Leu Gln Gln
545                 550                 555                 560

Gln Leu Gln Ser Lys Glu Glu Lys Glu Leu Val Gln Ser Phe
                565                 570                 575

Glu Leu Lys Ile Ala Glu Leu Glu Gln Leu Ser Val Lys Ala Lys
                580                 585                 590

Asn Leu Glu Met Val Thr Asn Ser Arg Glu His Ser Ile Asn Ala Glu
                595                 600                 605

Val Gln Thr Asp Val Glu Lys Glu Val Val Arg Lys Glu Met Ser Val
610                 615                 620

Leu Gly Asp Ser Gly Tyr Asn Ala Ser Asn Ser Asp Leu Gln Asp Ser
625                 630                 635                 640

Ser Val Asp Gly Lys Arg Leu Ser Ser His Asp Glu Cys Ile Glu
                645                 650                 655

His Arg Lys Met Leu Glu Gln Lys Ile Val Asp Leu Glu Glu Phe Ile
                660                 665                 670

Glu Asn Leu Asn Lys Lys Ser Glu Asn Asp Lys Gln Lys Ser Ser Glu
                675                 680                 685

Gln Asp Phe Met Glu Ser Ile Gln Leu Cys Glu Ala Ile Met Ala Glu
                690                 695                 700

Lys Ala Asn Ala Leu Glu Glu Leu Ala Leu Met Arg Asp Asn Phe Asp
705                 710                 715                 720

Asn Ile Ile Leu Glu Asn Glu Thr Leu Lys Arg Glu Ile Ala Asp Leu
                725                 730                 735

Glu Arg Ser Leu Lys Glu Asn Gln Glu Thr Asn Glu Phe Glu Ile Leu
                740                 745                 750

Glu Lys Glu Thr Gln Lys Glu His Glu Ala Gln Leu Ile His Glu Ile
                755                 760                 765

Gly Ser Leu Lys Lys Leu Val Glu Asn Ala Glu Met Tyr Asn Gln Asn
770                 775                 780

Leu Glu Glu Asp Leu Glu Thr Lys Thr Lys Leu Leu Lys Glu Gln Glu
785                 790                 795                 800

Ile Gln Leu Ala Glu Leu Arg Lys Arg Ala Asp Asn Leu Gln Lys Lys
                805                 810                 815

Val Arg Asn Phe Asp Leu Ser Val Ser Met Gly Asp Ser Glu Lys Leu
                820                 825                 830

Cys Glu Glu Ile Phe Gln Leu Lys Gln Ser Leu Ser Asp Ala Glu Ala
                835                 840                 845

Val Thr Arg Asp Ala Gln Lys Glu Cys Ser Phe Leu Arg Ser Glu Asn
                850                 855                 860

Leu Glu Leu Lys Glu Lys Met Glu Asp Thr Ser Asn Trp Tyr Asn Gln
865                 870                 875                 880
```

-continued

Lys Glu Lys Ala Ala Ser Leu Phe Glu Lys Gln Leu Glu Thr Glu Lys
                885                 890                 895

Ser Asn Tyr Lys Lys Met Glu Ala Asp Leu Gln Lys Glu Leu Gln Ser
            900                 905                 910

Ala Phe Asn Glu Ile Asn Tyr Leu Asn Gly Leu Leu Ala Gly Lys Val
        915                 920                 925

Pro Arg Asp Leu Leu Ser Arg Val Glu Leu Glu Lys Lys Val Ser Glu
    930                 935                 940

Phe Ser Lys Gln Leu Glu Lys Ala Leu Glu Glu Lys Asn Ala Leu Glu
945                 950                 955                 960

Asn Glu Val Thr Cys Leu Ser Glu Tyr Lys Phe Leu Pro Asn Glu Val
                965                 970                 975

Glu Cys Leu Lys Asn Gln Ile Ser Lys Ala Ser Glu Glu Ile Met Leu
            980                 985                 990

Leu Lys Gln Glu Gly Glu His Ser Ala Ser Ile Ile Ser Lys Gln Glu
        995                 1000                1005

Ile Ile Met Gln Glu Gln Ser Glu Gln Ile Leu Gln Leu Thr Asp Glu
    1010                1015                1020

Val Thr His Thr Gln Ser Lys Val Gln Gln Thr Glu Glu Gln Tyr Leu
1025                1030                1035                1040

Glu Met Lys Lys Met His Asp Asp Leu Phe Glu Lys Tyr Ile Arg Asn
                1045                1050                1055

Lys Ser Glu Ala Glu Asp Leu Leu Arg Glu Met Glu Asn Leu Lys Gly
            1060                1065                1070

Thr Met Glu Ser Val Glu Val Lys Ile Ala Asp Thr Lys His Glu Leu
        1075                1080                1085

Glu Glu Thr Ile Arg Asp Lys Glu Gln Leu Leu His Glu Lys Lys Tyr
    1090                1095                1100

Phe Phe Gln Ala Met Gln Thr Ile Phe Pro Ile Thr Pro Leu Ser Asp
1105                1110                1115                1120

Ser Leu Pro Pro Ser Lys Leu Val Glu Gly Asn Ser Gln Asp Pro Ile
                1125                1130                1135

Glu Ile Asn Asp Tyr His Asn Leu Ile Ala Leu Ala Thr Glu Arg Asn
            1140                1145                1150

Asn Ile Met Val Cys Leu Glu Thr Glu Arg Asn Ser Leu Lys Glu Gln
        1155                1160                1165

Val Ile Asp Leu Asn Thr Gln Leu Gln Ser Leu Gln Ala Gln Ser Ile
    1170                1175                1180

Glu Lys Ser Asp Leu Gln Lys Pro Lys Gln Asp Leu Glu Glu Gly Glu
1185                1190                1195                1200

Val Lys Leu Leu Leu Glu Met Glu Leu Leu Lys Gly His Leu Thr Asp
                1205                1210                1215

Ser Gln Leu Ser Ile Glu Lys Leu Gln Leu Glu Asn Leu Glu Val Thr
            1220                1225                1230

Glu Lys Leu Gln Thr Leu Gln Glu Met Lys Asn Ile Thr Ile Glu
        1235                1240                1245

Arg Asn Glu Leu Gln Thr Asn Phe Glu Asp Leu Lys Ala Glu His Asp
    1250                1255                1260

Ser Leu Lys Gln Asp Leu Ser Glu Asn Ile Glu Gln Ser Ile Glu Thr
1265                1270                1275                1280

Gln Asp Glu Leu Arg Ala Ala Gln Glu Glu Leu Arg Glu Gln Lys Gln
                1285                1290                1295

-continued

```
Leu Val Asp Ser Phe Arg Gln Gln Leu Leu Asp Cys Ser Val Gly Ile
        1300                1305                1310
Ser Ser Pro Asn His Asp Ala Val Ala Asn Gln Glu Lys Val Ser Leu
        1315                1320                1325
Gly Glu Val Asn Ser Leu Gln Ser Glu Met Leu Arg Gly Glu Arg Asp
    1330                1335                1340
Glu Leu Gln Thr Ser Cys Lys Ala Leu Val Ser Glu Leu Glu Leu Leu
1345                1350                1355                1360
Arg Ala His Val Lys Ser Val Glu Gly Glu Asn Leu Glu Ile Thr Lys
        1365                1370                1375
Lys Leu Asn Gly Leu Glu Lys Glu Ile Leu Gly Lys Ser Glu Glu Ser
        1380                1385                1390
Glu Val Leu Lys Ser Met Leu Glu Asn Leu Lys Glu Asp Asn Asn Lys
        1395                1400                1405
Leu Lys Glu Gln Ala Glu Glu Tyr Ser Ser Lys Glu Asn Gln Phe Ser
        1410                1415                1420
Leu Glu Glu Val Phe Ser Gly Ser Gln Lys Leu Val Asp Glu Ile Glu
1425                1430                1435                1440
Val Leu Lys Ala Gln Leu Lys Ala Ala Glu Glu Arg Leu Glu Ile Lys
        1445                1450                1455
Asp Arg Asp Tyr Phe Glu Leu Val Gln Thr Ala Asn Thr Asn Leu Val
        1460                1465                1470
Glu Gly Lys Leu Glu Thr Pro Leu Gln Ala Asp His Glu Glu Asp Ser
        1475                1480                1485
Ile Asp Arg Arg Ser Glu Glu Met Glu Ile Lys Val Leu Gly Glu Lys
        1490                1495                1500
Leu Glu Arg Asn Gln Tyr Leu Leu Glu Arg Leu Gln Glu Glu Lys Leu
1505                1510                1515                1520
Glu Leu Ser Asn Lys Leu Glu Ile Leu Gln Lys Glu Met Glu Thr Ser
        1525                1530                1535
Val Leu Lys Asp Asp Leu Gln Gln Lys Leu Glu Ser Leu Leu Ser
        1540                1545                1550
Glu Asn Ile Ile Leu Lys Glu Asn Ile Asp Thr Thr Leu Lys His His
        1555                1560                1565
Ser Asp Thr Gln Ala Gln Leu Gln Lys Thr Gln Gln Glu Leu Gln Leu
        1570                1575                1580
Ala Lys Asn Leu Ala Ile Ala Ala Ser Asp Asn Cys Pro Ile Thr Gln
1585                1590                1595                1600
Glu Lys Glu Thr Ser Ala Asp Cys Val His Pro Leu Glu Glu Lys Ile
        1605                1610                1615
Leu Leu Leu Thr Glu Glu Leu His Gln Lys Thr Asn Glu Gln Glu Lys
        1620                1625                1630
Leu Leu His Glu Lys Asn Glu Leu Glu Gln Ala Gln Val Glu Leu Lys
        1635                1640                1645
Cys Glu Val Glu His Leu Met Lys Ser Met Ile Glu Ser Lys Ser Ser
        1650                1655                1660
Leu Glu Ser Leu Gln His Glu Lys His Asp Thr Glu Gln Gln Leu Leu
1665                1670                1675                1680
Ala Leu Lys Gln Gln Met Gln Val Val Thr Gln Glu Lys Lys Glu Leu
        1685                1690                1695
Gln Gln Thr His Glu His Leu Thr Ala Glu Val Asp His Leu Lys Glu
        1700                1705                1710
Asn Ile Glu Leu Gly Leu Asn Phe Lys Asn Glu Ala Gln Gln Lys Thr
```

-continued

```
                 1715                1720                1725
Thr Lys Glu Gln Cys Leu Leu Asn Glu Asn Lys Glu Leu Glu Gln Ser
     1730                1735                1740
Gln His Arg Leu Gln Cys Glu Ile Glu Glu Leu Met Lys Ser Leu Lys
 1745                1750                1755                1760
Asp Lys Glu Ser Ala Leu Glu Thr Leu Lys Glu Ser Glu Gln Lys Val
             1765                1770                1775
Ile Asn Leu Asn Gln Glu Met Glu Met Val Met Leu Glu Met Glu Glu
         1780                1785                1790
Leu Lys Asn Ser Gln Arg Thr Val Ile Ala Glu Arg Asp Gln Leu Gln
     1795                1800                1805
Asp Asp Leu Arg Glu Ser Val Glu Met Ser Ile Glu Thr Gln Asp Asp
 1810                1815                1820
Leu Arg Lys Ala Gln Glu Ala Leu Gln Gln Gln Lys Asp Lys Val Gln
 1825                1830                1835                1840
Glu Leu Thr Ser Gln Ile Ser Val Leu Gln Glu Lys Ile Ser Leu Leu
             1845                1850                1855
Glu Asn Gln Met Leu Tyr Asn Val Ala Thr Val Lys Glu Thr Leu Ser
         1860                1865                1870
Glu Arg Asp Asp Leu Asn Gln Ser Lys Gln His Leu Phe Ser Glu Ile
     1875                1880                1885
Glu Thr Leu Ser Leu Ser Leu Lys Glu Lys Glu Phe Ala Leu Glu Gln
 1890                1895                1900
Ala Glu Lys Asp Lys Ala Asp Ala Ala Arg Lys Thr Ile Asp Ile Thr
 1905                1910                1915                1920
Glu Lys Ile Ser Asn Ile Glu Glu Gln Leu Leu Gln Gln Ala Thr Asn
             1925                1930                1935
Leu Lys Glu Thr Leu Tyr Glu Arg Glu Ser Leu Ile Gln Cys Lys Glu
         1940                1945                1950
Gln Leu Ala Leu Asn Thr Glu His Leu Arg Glu Thr Leu Lys Ser Lys
     1955                1960                1965
Asp Leu Ala Leu Gly Lys Met Glu Gln Glu Arg Asp Glu Ala Ala Asn
 1970                1975                1980
Lys Val Ile Ala Leu Thr Glu Lys Met Ser Ser Leu Glu Glu Gln Ile
 1985                1990                1995                2000
Asn Glu Asn Val Thr Thr Leu Lys Glu Gly Glu Gly Glu Lys Glu Thr
             2005                2010                2015
Phe Tyr Leu Gln Arg Pro Ser Lys Gln Gln Ser Ser Ser Gln Met Glu
         2020                2025                2030
Glu Leu Arg Glu Ser Leu Lys Thr Lys Asp Leu Gln Leu Glu Glu Ala
     2035                2040                2045
Glu Lys Glu Ile Ser Glu Ala Thr Asn Glu Ile Lys Asn Leu Thr Ala
 2050                2055                2060
Lys Ile Ser Ser Leu Glu Glu Glu Ile Leu Gln Asn Ala Ser Ile Leu
 2065                2070                2075                2080
Asn Glu Ala Val Ser Glu Arg Glu Asn Leu Arg His Ser Lys Gln Gln
             2085                2090                2095
Leu Val Ser Glu Leu Glu Gln Leu Ser Leu Thr Leu Lys Ser Arg Asp
         2100                2105                2110
His Ala Phe Ala Gln Ser Lys Arg Glu Lys Asp Glu Ala Val Asn Lys
     2115                2120                2125
Ile Ala Ser Leu Ala Glu Glu Ile Lys Ile Leu Thr Lys Glu Met Asp
 2130                2135                2140
```

-continued

```
Glu Phe Arg Asp Ser Lys Glu Ser Leu Gln Glu Gln Ser Ser His Leu
2145                2150                2155                2160

Ser Glu Glu Leu Cys Thr Tyr Lys Thr Glu Leu Gln Met Leu Lys Gln
            2165                2170                2175

Gln Lys Glu Asp Ile Asn Asn Lys Leu Ala Glu Lys Val Lys Glu Val
        2180                2185                2190

Asp Glu Leu Leu Gln His Leu Ser Ser Leu Lys Glu Gln Leu Asp Gln
    2195                2200                2205

Ile Gln Met Glu Leu Arg Asn Glu Lys Leu Arg Asn Tyr Glu Leu Cys
2210                2215                2220

Glu Lys Met Asp Ile Met Glu Lys Glu Ile Ser Val Leu Arg Leu Met
2225                2230                2235                2240

Gln Asn Glu Pro Gln Gln Glu Glu Asp Asp Val Ala Glu Arg Met Asp
            2245                2250                2255

Ile Leu Glu Ser Arg Asn Gln Glu Ile Gln Glu Leu Met Glu Lys Ile
        2260                2265                2270

Ser Ala Val Tyr Ser Glu Gln His Thr Leu Leu Ser Ser Leu Ser Ser
    2275                2280                2285

Glu Leu Gln Lys Glu Thr Glu Ala His Lys His Cys Met Leu Asn Ile
2290                2295                2300

Lys Glu Ser Leu Ser Ser Thr Leu Ser Arg Ser Phe Gly Ser Leu Gln
2305                2310                2315                2320

Thr Glu His Val Lys Leu Asn Thr Gln Leu Gln Thr Leu Leu Asn Lys
            2325                2330                2335

Phe Lys Val Val Tyr Arg Thr Ala Ala Val Lys Glu Asp His Ser Leu
        2340                2345                2350

Ile Lys Asp Tyr Glu Lys Asp Leu Ala Ala Glu Gln Lys Arg His Asp
    2355                2360                2365

Glu Leu Arg Leu Gln Leu Gln Cys Leu Glu Gln His Gly Arg Lys Trp
2370                2375                2380

Ser Asp Ser Ala Ser Glu Glu Leu Lys Phe Cys Glu Ile Glu Phe Leu
2385                2390                2395                2400

Asn Glu Leu Leu Phe Lys Lys Ala Asn Ile Ile Gln Ser Val Gln Asp
            2405                2410                2415

Asp Phe Ser Glu Val Gln Val Phe Leu Asn Gln Val Gly Ser Thr Leu
        2420                2425                2430

Gln Glu Glu Leu Glu His Lys Lys Gly Phe Met Gln Trp Leu Glu Glu
    2435                2440                2445

Phe Gly Asp Leu His Val Asp Ala Lys Lys Leu Ser Glu Gly Met Gln
2450                2455                2460

Gln Glu Asn Arg Arg Ile Ala Ser Thr Ile Gln Leu Leu Thr Lys Arg
2465                2470                2475                2480

Leu Lys Ala Val Val Gln Ser Lys Ile Gln Arg Glu Ile Thr Val Tyr
            2485                2490                2495

Leu Asn Gln Phe Glu Ala Lys Leu Gln Glu Lys Lys Glu Gln Asn Lys
        2500                2505                2510

Glu Leu Met Arg Arg Met Glu His His Gly Pro Ser Ala Ser Val Met
    2515                2520                2525

Glu Glu Glu Asn Ala Arg Leu Leu Gly Ile Leu Lys Thr Val Gln Asp
2530                2535                2540

Glu Ser Lys Lys Leu Gln Ser Arg Ile Lys Met Leu Glu Asn Glu Leu
2545                2550                2555                2560
```

-continued

```
Asn Leu Val Lys Asp Asp Ala Met His Lys Gly Glu Lys Val Ala Ile
            2565                2570                2575
Leu Gln Asp Lys Leu Leu Ser Arg Asn Ala Glu Ala Glu Leu Asn Ala
        2580                2585                2590
Met Gln Val Lys Leu Thr Lys Lys Gln Asp Asn Leu Gln Ala Ala Met
    2595                2600                2605
Lys Glu Ile Glu Asn Leu Gln Lys Met Val Ala Lys Gly Ala Val Pro
    2610                2615                2620
Tyr Lys Glu Glu Ile Asp Asn Leu Lys Thr Lys Val Lys Ile Glu
2625                2630                2635                2640
Met Glu Lys Ile Lys Tyr Ser Lys Ala Thr Asp Gln Glu Ile Ala Tyr
            2645                2650                2655
Leu Lys Ser Cys Leu Glu Asp Lys Glu Glu Gly Leu Arg Arg Leu Lys
            2660                2665                2670
Glu Glu Leu Arg Arg Ala Gln Ala Asp Asn Asp Thr Thr Val Cys Val
        2675                2680                2685
Pro Lys Asp Tyr Gln Lys Ala Ser Thr Phe Pro Val Thr Cys Gly Gly
    2690                2695                2700
Gly Ser Gly Ile Val Gln Ser Thr Ala Met Leu Val Leu Gln Ser Glu
2705                2710                2715                2720
Lys Ala Ala Leu Glu Arg Glu Leu Ser His Tyr Lys Lys Lys Tyr His
            2725                2730                2735
His Leu Ser Arg Thr Met Ser Ser Ser Glu Asp Arg Lys Lys Thr Lys
            2740                2745                2750
Ala Lys Ser Asp Ala His Ser Ser His Thr Gly Ser Ser His Arg Gly
        2755                2760                2765
Ser Pro His Lys Thr Glu Thr Tyr Arg His Gly Pro Val Thr Pro Glu
    2770                2775                2780
Arg Ser Glu Met Pro Ser Leu His Leu Gly Ser Pro Lys Lys Ser Glu
2785                2790                2795                2800
Ser Ser Thr Lys Arg Val Val Ser Pro Asn Arg Ser Glu Ile Tyr Ser
            2805                2810                2815
Gln Leu Val Met Ser Pro Gly Lys Thr Gly Met His Lys His Ile Leu
            2820                2825                2830
Ser Pro Ser Lys Val Gly Leu His Lys Lys Arg Ala Leu Ser Pro Asn
        2835                2840                2845
Arg Ser Glu Met Pro Thr Gln His Val Ile Ser Pro Gly Lys Thr Gly
    2850                2855                2860
Leu His Lys Asn Leu Thr Glu Ser Thr Leu Phe Asp Asn Leu Ser Ser
2865                2870                2875                2880
Pro Cys Lys Gln Gln Lys Val Gln Glu Asn Leu Asn Ser Pro Lys Gly
            2885                2890                2895
Lys Leu Phe Asp Val Lys Ser Lys Ser Met Pro Tyr Cys Pro Ser Gln
            2900                2905                2910
Phe Phe Asp Asn Ser Lys Leu Gly Asp Phe Ser Glu Leu Asn Thr Ala
        2915                2920                2925
Glu Ser Asn Asp Lys Ser Gln Ala Glu Asn Trp Trp Tyr Glu Ala Lys
    2930                2935                2940
Lys Glu Thr Ala Pro Glu Cys Lys Thr Ser
2945                2950

<210> SEQ ID NO 2
<211> LENGTH: 9626
<212> TYPE: DNA
```

<213> ORGANISM: Xenopus sp.
<220> FEATURE:
<223> OTHER INFORMATION: XCENP-E nucleotide sequence
<220> FEATURE:
<221> NAME/KEY: CDS
<222> LOCATION: (143)..(9007)

<400> SEQUENCE: 2

| | | | | | |
|---|---|---|---|---|---|
| gaattccgga | gtcggatagg | ctagtcgggc | gagggaaatt | caaactggtt | atagaagaaa | 60 |
| cttgaaccgc | cgccaaaagg | gactaaagtg | acagagacag | ggagcggtgt | cggtaccgat | 120 |
| ttctccacta | atcggtctca | aaatgtccga | gggagatgca | gttaaagtgt | gtgtgagggt | 180 |
| tcggccgctt | atacagagag | aacaagggga | tcaagccaac | ctgcaatgga | aggctggaaa | 240 |
| caacaccatt | tcccaagttg | atgggacaaa | gtctttcaat | ttcgatcgtg | tatttaattc | 300 |
| tcacgaatca | acaagtcaaa | tttaccaaga | aatagcagta | cctatcatac | gatcagcttt | 360 |
| gcagggatat | aatggcacaa | tatttgcata | cggacagaca | tcttcaggca | agacgtacac | 420 |
| aatgatggga | acaccaaatt | cattgggcat | aatacccaa | gccatacagg | aagttttaa | 480 |
| aattattcag | gagataccga | acagagagtt | tcttctaaga | gtttcttata | tggagattta | 540 |
| caatgaaact | gtgaaagacc | tactgtgtga | tgacagaaga | aagaagccct | tggaaattcg | 600 |
| cgaggatttt | aatagaaacg | tgtatgttgc | tgacctgact | gaagaacttg | taatggttcc | 660 |
| tgaacatgta | atacagtgga | tcaaaaaggg | tgaaaaaaac | agacattatg | gagagactaa | 720 |
| aatgaatgat | catagtagtc | gttcacatac | aatatttaga | atgattgttg | aaagccgaga | 780 |
| cagaaatgat | cccacaaatt | cagagaactg | tgatggagct | gtcatggtat | ctcacttgaa | 840 |
| tttggtagat | cttgctggca | gtgaaagagc | aagccaaact | ggagctgaag | gtgtgagact | 900 |
| taaggaaggc | tgcaacatca | accgcagctt | gtttatcctt | ggacaggtta | ttaagaagct | 960 |
| tagcgacggc | caggctggtg | gatttataaa | ctacagagac | agcaaactca | ccagaattct | 1020 |
| ccaaaattca | ttgggaggaa | atgctaaaac | ggttataatt | tgcacaatta | cgccagtttc | 1080 |
| ttttgatgag | actctaagta | cacttcagtt | tgccagtact | gccaaacatg | tgagaaatac | 1140 |
| tccccatgtt | aatgaggtcc | tggatgatga | agcgttgcta | aaaaggtaca | gaaggaaat | 1200 |
| cttggattta | agaaacaat | tagagaattt | agagtcatcg | tctgaaacaa | aagctcaagc | 1260 |
| aatggctaaa | gaagagcata | cacagttgct | agctgaaatc | aaacaactac | acaaagagag | 1320 |
| agaagataga | atatggcact | tgacaaatat | tgttgttgct | tcatcccaag | aatctcaaca | 1380 |
| ggaccaaagg | gtcaaacgaa | aacgaagagt | tacgtgggcg | ccaggaaaaa | tccaaaatag | 1440 |
| tttacatgct | tctggtgttt | ctgactttga | tatgctatcc | agattacctg | gcaattttag | 1500 |
| caagaaggca | aagttctctg | acatgccttc | atttccagaa | attgatgact | ctgtttgtac | 1560 |
| agagttttct | gattttgatg | acgccctctc | catgatggac | agcaatggaa | tagatgcaga | 1620 |
| atggaattta | gccagtaaag | taactcacag | agaaaagaca | tcacttcatc | aatcaatgat | 1680 |
| agactttgga | cagatttctg | acagtgttca | gtttcatgat | tcttctaagg | aaaaccagct | 1740 |
| acaatacctc | cccaaagact | ctggtgatat | ggctgaatgc | agaaaagctt | cttttgaaaa | 1800 |
| agagatcaca | agcctccagc | aacaactaca | gtcaaaggag | gaagaaaaaa | aggaacttgt | 1860 |
| acaaagcttc | gagctcaaga | tagcagaact | ggaagagcag | cttagtgtca | aagctaaaaa | 1920 |
| tctagagatg | gttacaaact | cgagagagca | ttccattaat | gctgaagtcc | aaacagatgt | 1980 |
| tgaaaaggaa | gttgtgagaa | agaaatgtc | agtccttgga | gactctggtt | acaatgcatc | 2040 |
| aaacagtgac | ctacaggata | gttctgttga | tggtaaacgt | ctaagcagct | cccatgatga | 2100 |

```
gtgtatagaa cacagaaaaa tgctggaaca aaagatcgtt gatttagaag agtttattga    2160
aaaccttaac aagaaaagtg agaatgataa acaaaaatct tctgagcaag attttatgga    2220
gagtattcag ctatgtgaag ctataatggc agaaaaggca aatgcactgg aggaactggc    2280
acttatgcga gataattttg acaatattat tctagagaat gaaactctaa aagggaaat     2340 tgcagatctg gaacgttcac tcaaggagaa tcaagaaacc aatgagtttg aaattctgga    2400
gaaggaaact caaaagaac acgaggcaca actaatccat gagattggca gtttaaagaa     2460
attagttgaa aatgcagaga tgtacaatca aaatcttgag gaagatctag aaactaaaac    2520
aaaacttctg aaagagcagg aaattcaact tgcagaatta aggaaacgcg cagataactt    2580
gcagaaaaaa gtacgaaatt ttgatctctc ggtttccatg ggtgatagtg agaaactctg    2640
tgaagaaatc tttcaactga agcaatctct ttctgatgct gaagctgtga ctcgcgatgc    2700
tcagaaggaa tgttctttcc tcagaagtga aaatctagag ctgaaggaga aaatggagga    2760
cacatcaaac tggtacaatc aaaaagaaaa ggctgcgtct ttgtttgaga agcagctgga    2820
aactgaaaaa tcaaactaca agaaaatgga agctgatttg cagaaagagt tgcaaagtgc    2880
ttttaatgag attaactact taaatggcct tctggcagga aaggtcccca gagatttgct    2940
ttctcgtgtt gaattagaga aaaaggtttc tgagttctca aagcagcttg agaaagcatt    3000
ggaagaaaaa aatgccttgg agaatgaagt gacttgccta tcagaataca aattttttgcc   3060 aaatgaagtt gaatgcttga aaaatcagat cagcaaggct tctgaagaga taatgttatt    3120
aaagcaagaa ggagaacatt ctgcatctat tataagcaaa caagagatta tcatgcagga    3180
gcaatctgag cagattttac aactgactga cgaagtgaca cacacacagt caaaagtgca    3240
gcagactgaa gagcaatact tggagatgaa gaaaatgcat gatgatcttt ttgaaaagta    3300
tatcagaaac aaaagtgaag ctgaagacct tttaagagaa atggagaacc ttaaaggcac    3360
tatggagtct gtggaagtaa agattgctga cacaaaacat gaacttgaag aaactataag    3420
ggataaggag caactgcttc atgagaaaaa atactttttt caagcaatgc agactatatt    3480
tccgattaca cctctttcag actcgcttcc tccctcaaaa ttagttgaag ggaactctca    3540
agaccccata gaaatcaatg actaccacaa tttaatagcc cttgctacag aaaggaacaa    3600
cattatggtg tgtctagaga ctgaaagaaa cagtctcaag gagcaagtta ttgatttgaa    3660
cactcaactt caaagtcttc aagcacaaag tattgaaaag tctgatctcc agaagccaaa    3720
gcaagacttg gaagaaggag aggttaaact gcttttggag atggaactac tgaagggaca    3780
cctaactgac tcacagctgt ctatagagaa attgcagctg gagaatctgg aagttacaga    3840
aaaactccaa acacttcaag aagagatgaa aaatattact atagaaagga atgagcttca    3900
gaccaacttc gaagacctga agcagagca tgatagccta aaacaagacc ttagtgaaaa     3960
cattgagcag tcaattgaaa cacaagatga attaagggct gcccaggaag agctaagaga    4020
acagaagcaa ctggttgata gctttagaca acagcttta gattgttctg taggaatttc    4080
atcaccaaac catgatgcag ttgctaacca ggaaaaggtg tcattgggtg aagttaattc     4140
gttacaaagt gaaatgctgc gtggtgaaag agatgagctt caaacatctt gtaaggcatt    4200
agtttcagaa ctggagctac ttcgtgctca tgtaaaatct gtggagggag aaaaccttga    4260
aatcacaaaa aaactcaatg gccttgaaaa ggagatattg gcaaatctg aagaaagcga      4320 agtgttgaag tccatgttgg agaatctaaa ggaagacaac aataagctca agaacaagc     4380 agaggaatat tctagtaaag aaaatcaatt cagtttagaa gaggtgttca gtggttcaca    4440
gaagctggta gatgagatag aggtcctgaa agcacagcta aaggcagcag aagaaaggct    4500
```

```
ggaaataaag gatagagatt attttgaact tgtacaaact gcaaacacca atttagttga  4560
gggaaaattg gaaactccat tgcaagctga ccatgaggaa gacagcattg atcggcgttc  4620
tgaagaaatg gagataaaag ttcttggaga aaaacttgag cgaaatcagt atttactgga  4680
aagattgcaa gaagaaaagc tggaactgtc taacaaactt gaaatccttc agaaagagat  4740
ggagacgtcc gttctattaa aagatgacct gcaacagaag ctagaaagct tgctgagtga  4800
aaacattatt ctaaaagaga atattgacac aaccctaaag catcattcag atactcaagc  4860
tcagctgcag aaaacacagc aagagctaca gttggctaag aatcttgcaa tcgctgcttc  4920
tgacaattgt ccaataactc aagaaaagga aacctctgca gattgtgtgc atcctctgga  4980
agaaaagata ttgttattaa ctgaagaatt gcatcaaaaa actaatgaac aggaaaaatt  5040
actacatgaa aagaatgaac ttgaacaagc tcaggttgag ctaaagtgcg aggtggaaca  5100
tctgatgaag agtatgatcg aatcgaagtc ctcacttgag tccttgcagc atgagaaaca  5160
tgatactgaa caacaacttc ttgctcttaa acagcagatg caagtagtta ctcaagaaaa  5220
gaaagagctg caacaaaccc atgaacactt aacagctgag gtggaccatc taaaagagaa  5280
tattgaattg ggtttgaatt ttaaaaatga agcgcagcaa aagaccacta aagagcaatg  5340
tctgctaaat gagaataaag aacttgagca aagccagcac agacttcaat gtgagataga  5400
agagcttatg aaaagcttaa aggataaaga gtcagcgctg gaaactttaa aagaatctga  5460 acaaaagta attaatctga accaagaaat ggaaatggtt atgctggaaa tggaggaatt  5520
gaaaaatagc cagaggactg taattgctga gagggaccag ctgcaagacg acctaaggga  5580
gagtgttgaa atgtccattg aaactcaaga tgatctaaga aaggctcaag aagcattgca  5640
gcagcagaaa gataaagttc aggaactgac ctcccagatt tctgtcctgc aggaaaagat  5700
ctctcttctg gaaaatcaga tgctttataa tgttgcaact gtgaaagaaa ctctaagcga  5760
aagagatgac ctgaaccagt ctaagcaaca cctgttctca gaaattgaaa ctcttagtct  5820
gtctttaaaa gaaaaggaat ttgcattgga acaagcagag aaggacaaag ctgatgctgc  5880
caggaaaaca atagatatca cagagaagat atcaaatata gaagaacagt acttcaaca  5940 agccaccaat ttaaaggaaa ctctttatga agagagagt cttatccagt gtaaggagca  6000
actggctttg aacacagaac acctagggga acattgaag agcaaagact tggcattggg  6060
taaaatggag caggagagag atgaagctgc caataaagta atagctctta cagaaaagat  6120
gtcttctcta gaagaacaga tcaatgaaaa tgttactact ctaaaagaag gtgagggtga  6180
aaaagagacc ttctaccttc agagaccttc aaagcagcag tcttcttccc agatggaaga  6240
gctcagagag tctttaaaga ccaaagattt gcagttggaa gaggccgaga aggagataag  6300
tgaagctact aatgaaataa agaatctcac tgctaagatc tcttctctag aggaggagat  6360
tcttcagaat gctagcattt tgaatgaagc tgtaagcgaa agggaaaacc ttcgccattc  6420
gaagcagcaa ctggtttcag aattggagca gctatcactg acattaaaga gtagagacca  6480
tgcatttgcg caatctaaac gcgaaaagga tgaagctgta aataaaatag ccagtctcgc  6540
tgaagaaata aagatcctga caaaagagat ggatgaattc agagattcaa aggaatcctt  6600
gcaagaacag tcttcccatc taagtgaaga gttatgtaca tataagactg aacttcaaat  6660
gctcaagcaa cagaaagaag acatcaacaa caaacttgca gagaaagtta aggaagtgga  6720
tgagctattg caaacttat catctctaaa ggaacagctg gaccaaatac agatggagct  6780
aaggaatgaa aagctcagaa actatgaact ctgcgaaaag atggatatca tggaaaaaga  6840
```

```
aatctcagtg ctgcgtttaa tgcagaacga gcctcagcag gaagaagatg atgttgcaga    6900
acgtatggat atacttgaga gcagaaacca agaaatacag gagctgatgg aaaaaatctc    6960
cgctgtgtat tcagagcaac acactttgct cagcagtctc tctagtgagc ttcaaaagga    7020
aactgaagca cacaaacatt gcatgttaaa tataaaggaa tctctgtcat ccacgctctc    7080
cagatccttt ggcagcttgc aaactgagca tgttaagcta atactcaac tgcagaccct     7140
tctgaacaaa tttaaggttg tataccgaac tgctgcagtc aaagaagatc atagcttgat    7200
caaagattat gagaaggacc ttgctgctga gcaaaagagg catgatgagc tgcgactcca    7260
actgcagtgt ttggagcagc acggcagaaa atggtcggat tctgcatctg aggaactcaa    7320
gttctgtgaa attgaattct tgaatgagtt actttttaaa aaagcaaata taattcagag    7380
tgtccaggat gacttttcag aggtgcaggt attcctaaat caagtaggat caacactgca    7440
agaagagctt gagcacaaga aaggctttat gcagtggttg gaggaatttg gagatctgca    7500
cgtcgatgct aagaaactca gtgaaggcat gcaacaggaa aataggcgca ttgcttctac    7560
catacagctc ttaacaaaaa ggctaaaggc agttgttcag tcgaaaatac aacgtgagat    7620
aaccgtatat ctgaaccagt ttgaagcgaa attgcaagag aagaaagaac aaaacaaaga    7680
acttatgcgc agaatggagc accacggccc tagtgctagt gtaatggagg aagaaaatgc    7740
tagacttta ggcatactga aaactgttca agatgaatcc aagaaactcc aatcaaggat     7800
caaaatgcta gaaaatgaac tgaacttggt caaagatgat gccatgcaca aaggtgaaaa    7860
agttgcaatt ttgcaagaca aactactaag cagaaacgcc gaagctgagc taaacgcaat    7920
gcaggtgaaa ctaactaaaa agcaagataa tcttcaggct gcaatgaaag aaatagaaaa    7980
cctacagaaa atggttgcca aaggtgcagt accatataaa gaagaaattg acaaccttaa    8040
aactaaggtg gtaaagattg aaatggaaaa aataaagtac tcaaaagcaa cagaccaaga    8100
gattgcctac ttaaagtctt gttttggaaga taaggaagaa ggcttgcgta ggttaaaaga    8160
ggaacttagg cgagcacagg cagacaacga tacaacagtt tgtgttccaa aagattatca    8220
gaaagcttca actttccctg tgacttgtgg tggtggaagc ggtatagtgc agagcacagc    8280
aatgcttgtg ctgcagtcgg aaaaagccgc cttggaaagg gagctgtcac attataagaa    8340
gaaatatcat catttatcac ggactatgtc aagttctgaa gatcgaaaga aaacaaaggc    8400
aaaatctgat gctcattctt ctcatactgg atcatcacac agaggctcgc ctcacaaaac    8460
tgaaacttac agacatggcc ctgttactcc agaaaggtct gaaatgccaa gcctacacct    8520
aggatctcca aagaagtcgg agtccagcac taaacgtgtt gtgtcaccaa acaggtccga    8580
aatctcagc caattagtaa tgtctccagg caagaccggg atgcataaac atatactttc      8640
tccaagcaag gttggactgc acaaaaagcg tgccctgtct ccaaacagat cggagatgcc    8700
cacccagcat gtcatatccc ctggcaagac cggactgcat aaaaatctaa ctgaaagcac    8760
gttattcgac aatttgtctt ctccatgcaa acagcaaaaa gtacaggaaa atctaaattc    8820
ccctaaaggc aaattatttg atgtgaagtc aaaatcgatg ccttactgtc catctcagtt    8880
ttttgataat tctaagcttg gtgatttttc agagctcaac acagcagaga gcaatgacaa    8940
aagtcaggct gagaactggt ggtatgaagc aaaaaaagaa acggcacctg aatgtaaaac    9000
atcctagatc cctgtacatc tgactctcct gtcctgcaaa gagacttgct actctgcctt    9060
cttgtaggaa gaaacactag aaactgccat gtctgcataa aggagtctca ctggaagcaa    9120
aagttgttct ttagtagtaa tcactggttg ggcgagtggt tacgtctttta aaataaagtg    9180
caatacgtct cacgtctatt ttatatgtta tgtctgtgta tttgttacac ttttaagtcc    9240
```

-continued

```
cttgacttca tatttggctc atctgtagtt tctttgtgtt tgcgcacaca cacactggtg    9300
aaaaatgaca tttgcagtgt attgttttac tgactggtct ctctggggcc atccatgcaa    9360
agcaccatta gtgtgccaat gttttcact acttattatt atgtctgact ttgtgaaata     9420
gaaaatacta caaagatag ggcaaaagtt gttttctcac taggtaaacg atatgggttt     9480
aacttaatta ttctcctaat aaaatattct atataatggc atctcattag gtgacctaat    9540
ggttattctg cactcttgta aaccttttt aaatttcact cgtaataaag cagccctgat     9600
tttaaattaa aaaaaaacg gaattc                                          9626
```

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:9 amino acid
      insertion encoded by one cDNA isolated

<400> SEQUENCE: 3

Asn Ser Arg Glu His Ser Ile Asn Ala
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:putative
      nuclear localization signal (NLS)

<400> SEQUENCE: 4

Arg Lys Lys Thr Lys
 1               5

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 5
gggctgccca ggaagag                                                   17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 6
gacagcattg atcggcg                                                   17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 7
gagggttcgg ccgctta                                                   17

```
<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 8
tctggggcca tccatgc                                                  17

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 9
catatgacca tggccgaggg agatgcag                                      28

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 10
gtcaggtcag caacatacac g                                             21

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence:sequence
      linked at C-terminus of amino acids 1-473 of XCENP-E in plasmid
      pET23dXCEMycHis
<220> FEATURE:
<221> NAME/KEY: PEPTIDE
<222> LOCATION: (12)..(20)
<223> OTHER INFORMATION: c-myc epitope tag

<400> SEQUENCE: 11

Thr Val Ser Ile Ser Leu Gly Asp Leu Thr Met Glu Gln Lys Leu Ile
  1               5                  10                  15

Ser Glu Glu Asp Leu Asn Phe Glu His His His His His His
             20                  25                  30
```

PLUS END-DIRECTED MICROTUBULE MOTOR REQUIRED FOR CHROMOSOME CONGRESSION

CROSS REFERENCE TO RELATED APPLICATIONS

This is a Continuation of application Ser. No. 09/150,867, filed Sep. 10, 1998, which claims the benefit under 35 U.S.C. §119(e) to U.S. Provisional Patent Application Ser. No. 60/058,645, filed Sep. 11, 1997, herein incorporated by reference in its entirety.

FEDERALLY SPONSORED RESEARCH OR DEVELOPMENT

This invention was made with Government support under Grant Nos. GM35252 and GM 29513, awarded by the National Institutes of Health. The Government has certain rights in this invention.

FIELD OF THE INVENTION

The invention provides isolated nucleic acid and amino acid sequences of Xenopus CENP-E (XCENP-E), antibodies to XCENP-E, methods of screening for CENP-E modulators using biologically active CENP-E, and kits for screening for CENP-E modulators.

BACKGROUND OF THE INVENTION

Segregation of genetic material during mitosis is mediated by the microtubules of the mitotic spindle (see, e.g., McIntosh, in *Microtubules*, pp. 413–434 (Hyams & Lloyd, eds., 1994). During mitosis, chromosomes are dynamically attached to spindle microtubules via the kinetochore, which is a structure located at the centromere of the chromosome. Kinetochores are involved in coordinating chromosome movement via microtubule assembly and disassembly. The kinetochore and its component proteins thus play an important role in the dynamics of mitosis.

Spindle microtubules have a defined polarity, with their slow-growing, "minus" ends anchored at or near the spindle pole, and their dynamic, fast-growing "plus" ends interacting with chromosomes (McIntosh, et al., *J. Cell Biol.* 98:525–533 (1984)). During prometaphase, chromosomes establish interactions with the fast-growing plus ends of microtubules via the kinetochore. Chromosomes then undergo a series of microtubule-dependent movements, culminating in alignment at the metaphase plate, equidistant from the two spindle poles. This process is called "congression." However, the molecular mechanisms underlying chromosome congression are poorly understood (see, e.g., Rieder, et al., *J. Cell Biol.* 124:223–33 (1994)). A major question has been whether any kinetochore-associated microtubule motors play an important role in congression.

The two predominant and opposing forces are currently thought to be responsible for chromosome movement during congression: (1) an anti-poleward polar force associated with regions of high microtubule density near the spindle poles, and (2) a poleward force generated at the kinetochore (Khodjakov, et al., *J. Cell Biol.* 135:315–327 (1996); Waters, et al., *J. Cell Sci.* 109:2823–2831 (1996); reviewed in Rieder, et al., *Int. Rev. Cytol.* 79:1–57 (1982); Mitchison, et al., *Annu. Rev. Cell Biol.* 4:527–49 (1988); Rieder, et al., *J. Cell Biol.* 124:223–33 (1994)).

Studies in vitro have demonstrated the presence of both plus and minus end-directed microtubule motor activities on kinetochores that may be responsible for these chromosome movements (Mitchison, et al., *J. Cell Biol.* 101:766–77 (1985); Hyman, et al., *Nature* 351:206–211 (1991)). The outstanding issue, however, has been the identity of the molecules at the kinetochore which act as motors and generate the force for chromosome movement.

In general, both genetic and biochemical approaches have demonstrated crucial roles for microtubule motors in spindle assembly, spindle pole separation, and regulation of spindle microtubule dynamics. These motors include Eg5, CHO1/ MKlp1, ncd, cut7, bimC, CIN8, KIP1, KAR3, Xklp2, XKCM1, and XCTK2 (Sawin, et al., *Nature* 359:540–543 (1992); Blangy, et al., *Cell* 83:1159–1169 (1995); Sawin, et al., *J. Cell Biol.* 112:925–940 (1991); Nislow, et al., *J. Cell Biol.* 111:511–522 (1990); Endow, et al., *J. Cell Sci.* 107:859–867 (1994); Hagan, et al., *Nature* 347:563–566 (1990); Hagan, et al., *Nature* 356:74–76 (1992); Enos, et al., *Cell* 60:1019–1027 (1990); Hoyt, et al., *J. Cell Biol.* 118:109–120; Roof, et al., *J. Cell Biol.* 118:95–108 (1992); Saunders, et al., *Cell* 70:451–458 (1992), Boleti, et al., *J. Cell. Biol.* 125:1303–1312; Walczak, et al., *Cell* 84:37–47 (1996); Walczak, et al., *J. Cell Biol.* 136:859–70 (1997)). Two kinesin superfamily members, Xenopus Xklp1 and Drosophila nod localize to chromosome arms. With the exception of these two chromatin-associated motors, which are thought to mediate polar ejection forces, none of these other proteins have been implicated directly in congression or in chromosome movement during other phases of mitosis (Theurkauf, et al., *J. Cell Biol.* 116:1167–1180 (1992); Afshar, et al., *Cell* 81:129, *Cell* 81:128–138 (1995); Vernos, et al., *Trends in Cell Biol.* 5:297–301 (1995)).

A candidate for powering chromosome movement in mitosis is centromere-associated protein-E (CENP-E), a member of the kinesin superfamily of microtubule motor proteins. Human CENP-E has been cloned and is an integral component of the kinetochore (Yen, et al., *Nature* 359:536–539 (1992); Yao, et al., *The microtubule motor CENP-E is an integral component of kinetochore corona fibers that link centromeres to spindle microtubules* (manuscript)). CENP-E localizes to kinetochores throughout all phases of mitotic chromosome movement (early prometaphase through anaphase A) (Yen, et al., *Nature* 359:536–539 (1992); Brown, et al., *J. Cell. Biol.* 125:1303–1312 (1994); Lombillo, et al., *J. Cell Biol.* 128:107–115 (1995)).

Previous efforts have suggested a role for CENP-E in mitosis. Microinjection of a monoclonal antibody directed against CENP-E into cultured human cells delays anaphase onset (Yen, et al., *EMBO J.* 10:1245–1254 (1991)). Anti-CENP-E antibody injection into maturing mouse oocytes induces arrest at the first reductional division of meiosis (Duesbery, et al., *Proc. Natl. Acad. Sci. USA* (in press, 1997)). Antibodies against CENP-E block microtubule depolymerization-dependent minus end-directed movement of purified chromosomes in vitro (Lombillo, et al., *J. Cell Biol.* 128:107–115 (1995)).

However, these experiments have not demonstrated the precise role of CENP-E in mitosis, nor have they shown the activity of CENP-E, in particular any motor activity. Recently, CENP-E was reported to be associated with minus end-directed microtubule motor activity, raising the possibility that CENP-E might be responsible for poleward kinetochore movements (Thrower, et al., *EMBO J.* 14:918–926 (1995)). However, biologically active CENP-E has never been isolated, neither from naturally occurring nor recombinant sources.

SUMMARY OF THE INVENTION

The present invention provides for the first time biologically active CENP-E and surprisingly demonstrates, contrary to previous reports, that CENP-E is a motor that powers chromosome movement toward microtubule plus ends. Using immunodepletion and antibody addition to Xenopus egg extracts, the present invention further demonstrates that CENP-E plays an essential role in congression. The present invention also provides for the first time the nucleotide and amino acid sequence of isolated Xenopus CENP-E.

In one aspect, the invention provides an isolated, biologically active CENP-E protein, wherein the CENP-E protein has the following properties: (i) at least one activity selected from the group consisting of plus end-directed microtubule motor activity, ATPase activity, and microtubule binding activity; and (ii) the ability to specifically bind to polyclonal antibodies generated against CENP-E. In one embodiment, the CENP-E protein has an average molecular weight of about 300–350 kDa.

In one embodiment, the CENP-E protein has an amino acid sequence having at least 34%, or alternatively at least 45%, or alternatively at least 55% sequence identity with a XCENP-E motor domain of SEQ ID NO:1. Alternatively, CENP-E has at least 60%, 65% or 70% sequence identity with a XCENP-E motor domain of SEQ ID NO:1. In an alternative embodiment, the CENP-E has 70%, or alternatively 75%, or alternatively 80%, or alternatively 85%, or alternatively 90% or alternatively 95% amino acid sequence identity to a Xenopus CENP-E core motor domain as measured using a sequence comparison algorithm. In an alternative embodiment, the CENP-E protein has an amino acid sequence of SEQ ID NO:1.

In another embodiment provided herein, the CENP-E protein is encoded by a nucleic acid sequence having at least 70% sequence identity with SEQ ID NO:2. In another aspect of the present invention, the CENP-E protein is encoded by a nucleic acid which hybridizes under high stringency to a nucleic acid having a sequence complementary to that of SEQ ID NO:2.

In one embodiment, the CENP-E protein is from a human. In alternative embodiments provided herein, the CENP-E protein is from fungus, insects, or plants.

In an alternative embodiment provided herein, the CENP-E protein specifically binds to antibodies generated against Xenopus CENP-E (XCENP-E). In this embodiment, the CENP-E protein has an amino acid sequence having greater than 70%, or alternatively 75% sequence identity with a XCENP-E motor domain of SEQ ID NO:1. In another embodiment, the CENP-E protein has an amino acid sequence of a XCENP-E motor domain of SEQ ID NO:1.

In the embodiments wherein the CENP-E is biologically active as described herein, the amino acid sequence can have 74% or less sequence identity with the motor domain of SEQ ID NO:1.

Also provided herein is an isolated nucleic acid sequence encoding a CENP-E gene product, said sequence encoding a protein having a core motor domain that has greater than 70% or alternatively 75% amino acid sequence identity to a Xenopus CENP-E (XCENP-E) core motor domain as measured using a sequence comparison algorithm, and specifically binding to antibodies raised against CENP-E. In one embodiment, the sequence has a nucleotide sequence of SEQ ID NO:2. The sequence comparison algorithm can be PILEUP.

In another aspect of the invention, an antibody which specifically binds to CENP-E is provided.

Also provided herein is a method for identifying a candidate agent as a compound which modulates CENP-E activity. The method comprising the steps of determining CENP-E activity in the presence of a candidate agent at a control concentration. The CENP-E activity is selected from the group consisting of plus end-directed microtubule motor activity, ATPase activity and microtubule binding activity. The method further comprises the steps of determining said CENP-E activity in the presence the candidate agent at a test concentration, wherein a change in activity between the test concentration and the control concentration of said candidate agent indicates the identification of a compound which modulates CENP-E activity. The method can further comprise the step of isolating biologically active CENP-E from a cell sample.

The compound to be identified can be a lead therapeutic, bioagricultural compound or diagnostic. Preferably the compound is an antibody which specifically binds CENP-E. In one embodiment the method further comprises the step of modifying the antibody to be a humanized antibody. In one embodiment, the method is performed in a plurality such that many candidate agents are screened simultaneously.

The invention also includes kits for screening for modulators of CENP-E. The kit includes a container holding biologically active CENP-E and instructions for assaying for CENP-E activity, wherein the CENP-E activity is plus end-directed microtubule motor activity or ATPase activity.

The invention also provides a method of producing a biologically active CENP-E polypeptide. The method includes the steps of transforming a cell with a vector comprising the nucleic acid sequence encoding the motor domain of CENP-E; expressing said nucleic acid to produce a gene product; purifying said gene product; and identifying ATPase activity or plus-end directed microtubule activity of said gene product.

In another aspect of the invention, a method of moving microtubules in a plus ended direction is provided wherein microtubules are contacted with biologically active CENP-E.

In one embodiment the CENP-E is provided in gene form to a cell comprising microtubules.

BRIEF DESCRIPTION OF THE DRAWINGS

FIGS. 1A–C: Identification of Xenopus CENP-E

FIG. 1A: Structural comparison of Xenopus and human CENP-E. Hatched regions represent regions predicted to form a-helical coiled coils (Lupas, et al., *Science* 252, 1162–1164 (1991)). Within the N-terminal globular domains of both hCENP-E and XCENP-E there is a domain of ~324 amino acids corresponding to the kinesin like motor domain. Within these 324 amino acids XCENP-E and hCENP-E are 74% identical. One cDNA clone encoded a protein with a 9 amino acid insertion relative to the other cDNAs isolated (see Example I and methods). The position of this insertion is marked by the arrowhead. XCENP-E contains a putative nuclear localization signal (NLS) at the C-terminal end of the rod domain not present in hCENP-E.

FIG. 1B: XCENP-E fusion proteins used for polyclonal antibody production.

FIG. 1C: Deduced amino acid sequence of Xenopus CENP-E. cDNA sequence was compiled from 6 overlapping cDNA clones. Residues identical in hCENP-E and XCENP-E are shaded. The boxed region at the amino-terminus of the sequence is that portion of XCENP-E containing the motor domain and used to assay motility in vitro. The boxed sequence at the C-terminus is that portion of XCENP-E designated as the tail. The underlined sequence NSREHSINA (SEQ ID NO:3) at position 599 is the 9 amino acid relative insertion encoded by one of the cDNAs isolated (see FIG. 1A). The putative NLS, RKKTK (SEQ ID NO:4), immediately adjacent to the boxed tail domain is underlined.

FIG. 2A: Expression of recombinant XCENP-E in *E. coli*. XCENP-E amino acid residues 1-473 of XCENP-E were fused at the C-terminus to a c-myc epitope followed by a hexahistidine tag, expressed in *E. coli*, and purified over Ni-NTA-agarose resin. Coomassie stain of XCENP-E fusion protein used for motility (lane 1), immunoblot of XCENP-E fusion protein probed with α-myc monoclonal antibody (lane 2). Arrowheads indicate XCENP-E fusion protein.

FIG. 2B: XCENP-E Motility Assay. Microtubules marked near their minus ends with brightly fluorescent seeds were added with ATP to a flow chamber containing purified XCENP-E fusion protein tethered to the coverslip with a-myc monoclonal antibody. Gliding of microtubules was monitored by time-lapse digital fluorescence microscopy. Selected time points from one time lapse series, spaced 90 seconds apart are presented. As reference points, the positions of the plus ends of microtubules numbered 1, 2, and 3 at the start of continual gliding are marked with solid white dots, and the position of a stationary microtubule end is marked with an arrowhead. The bright seed of microtubule 3 enters the plane of focus at 1.5 minutes, and glides 13.6 $\mu$M downward with the bright seed leading over the following 3 minutes. Microtubule 2 moves continually during the first three minutes, after which point it detaches and reattaches further toward the bottom of the frame. Microtubule 1 glides minus-end leading throughout the entire time course. The average microtubule velocity of all microtubules was 5.1 $\mu$m/min±1.7 (n=49). Of those, 33 microtubules were unambiguously polarity marked, and all glided with their bright seeds leading. Scalebar is 5 $\mu$m.

DETAILED DESCRIPTION OF THE INVENTION

I. Introduction

The present invention provides for the first time biologically active CENP-E and demonstrates that CENP-E has a plus end-directed microtubule motor activity. Biologically active CENP-E was used to show that the kinesin-like motor domain of CENP-E powers chromosome movement toward microtubule plus ends. Finally, quantitative removal of Xenopus CENP-E ("XCENP-E") from Xenopus egg extracts normally capable of assembling mitotic spindles in vitro impairs congression of chromosomes to the metaphase plate. Together, these findings demonstrate that CENP-E plus-end directed microtubule motor activity in vivo is essential for congression during mitosis.

Figures 1A, 1B:
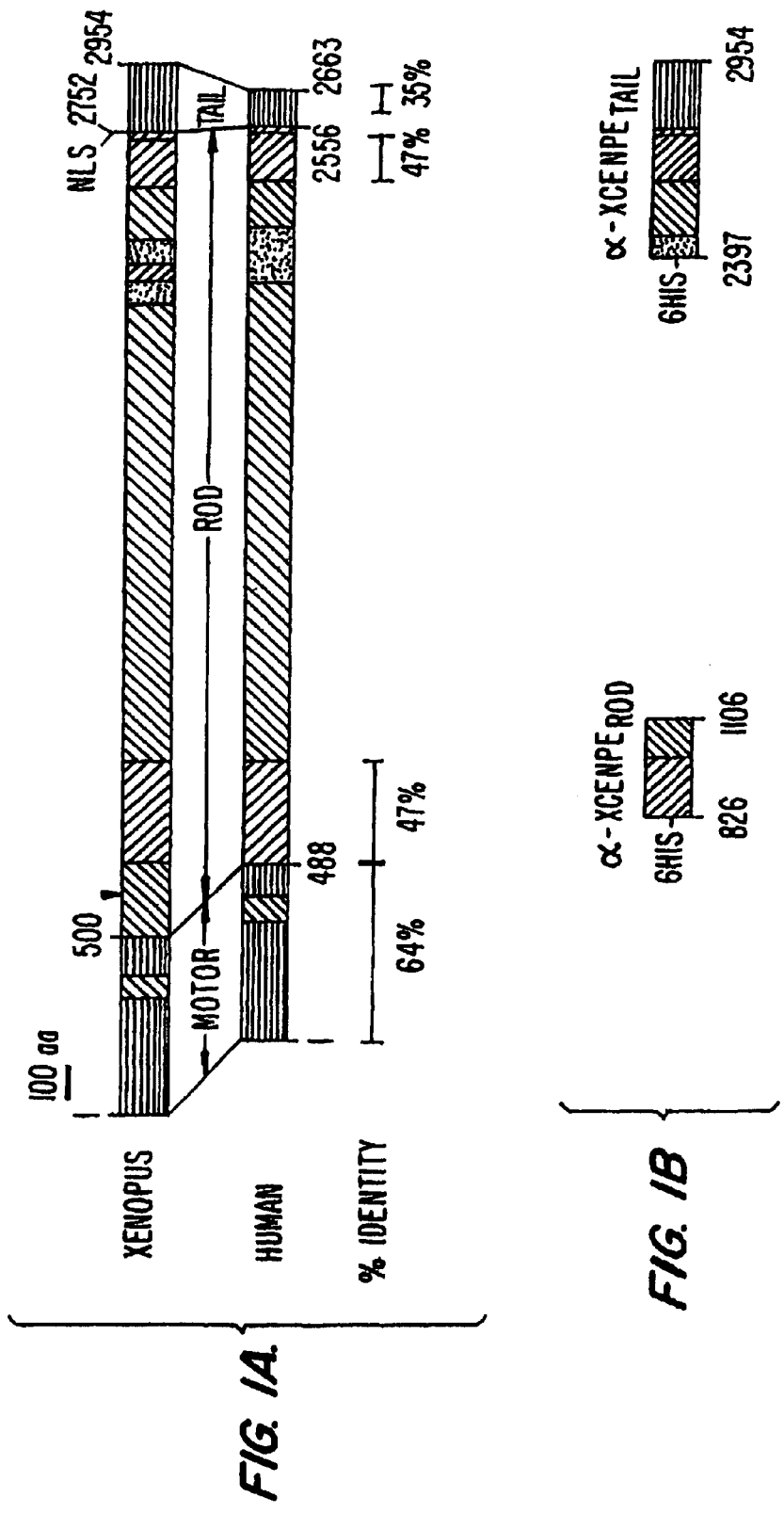

Functionally, CENP-E is localized in the kinetochores of condensed chromosomes in mitotic cells and has a plus-end directed microtubule motor activity that is ATP dependent (see, e.g., Example II, where ATP or another nucleotide triphosphate is included in the motility assay for motor activity). This activity is responsible for chromosome movement during mitosis. Structurally, the full length nucleotide sequence of XCENP-E (SEQ ID NO:2) encodes a protein of 2954 amino acids with a predicted molecular mass of 340 kDa (SEQ ID NO:1, FIG. 1C). XCENP-E is a member of the kinesin superfamily of motor proteins as evidenced by the sequence of its motor domain. The predicted structure of XCENP-E consists of a 500 amino acid globular amino-terminal domain containing a kinesin-like microtubule motor domain linked to a globular tail domain by a region predicted to form a long, discontinuous α-helical coiled coil (Lupas, et al., *Science* 252, 1162–1164 (1991); Berger, et al., *Proc. Natl. Acad. Sci. USA* 92:8259–8263 (1995)) (FIG. 1A). Within the core of the motor domain (residues 1–324) XCENP-E and human CENP-E ("hCENP-E") share 74% identity (Moore, et al., *Bioessays* 18:207–219 (1996)). Outside the amino-terminal domain lie three additional regions which share greater than 25% identity with hCENP-E, but not with other kinesin-like proteins (FIG. 1). CENP-E is found in Xenopus, mammalian cells, and is predicted to exist in some fungi and perhaps Drosophila.

The isolation of biologically active CENP-E for the first time provides a means for assaying for enhancers or inhibitors (i.e., modulators) of this essential mitotic protein. Biologically active CENP-E is useful for testing for enhancers or inhibitors using in vitro assays such as microtubule gliding assays (see, e.g., Example II) or ATPase assays (Kodama et al., *J. Biochem.* 99: 1465–1472 (1986); Stewart et al., *Proc. Nat'l Acad. Sci. USA* 90: 5209–5213 (1993); Sakowicz et al., *Science* 280:292–295 (1998)). For example, inhibitors identified using biologically active CENP-E can be used therapeutically to treat diseases of proliferating cells, including, e.g., cancers, hyperplasias, restenosis, cardiac hypertrophy, immune disorders, and inflammation. CENP-E also provides a convenient diagnostic marker for dividing cells. Antibodies or other probes for CENP-E can be used in vitro to identify cells that are entering mitosis. Inhibitors of CENP-E can also be used in vitro to synchronize cells just prior to entry into mitosis for use in cell culture.

II Definitions

As used herein, the following terms have the meanings ascribed to them unless specified otherwise.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated XCENP-E nucleic acid is separated from open reading frames which flank the XCENP-E gene and encode proteins other than XCENP-E. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Cassol et al., 1992; Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. A CENP-E polypeptide comprises a polypeptide demonstrated to have at least ATPase activity or plus end-directed microtubule motor activity and that binds to an antibody generated against CENP-E.

A "label" is a composition detectable by spectroscopic, photochemical, biochemical, immunochemical, or chemical means. For example, useful labels include $^{32}$p, fluorescent dyes, electron-dense reagents, enzymes (e.g., as commonly used in an ELISA), biotin, dioxigenin, or haptens and proteins for which antisera or monoclonal antibodies are available (e.g., the peptide of SEQ ID NO:1 can be made detectable, e.g., by incorporating a radio-label into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker, or through ionic, van der Waals or hydrogen bonds to a label such that the presence of the probe may be detected by detecting the presence of the label bound to the probe.

"Amplification" primers are oligonucleotides comprising either natural or analogue nucleotides that can serve as the basis for the amplification of a select nucleic acid sequence. They include, e.g., polymerase chain reaction primers and ligase chain reaction oligonucleotides.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. This definition also refers to the complement of a test sequence, which has a designated percent sequence or subsequence complementarity when the test sequence has a designated or substantial identity to a reference sequence. For example, a designated amino acid percent identity of 70% refers to sequences or subsequences that have at least about 70% amino acid identity when aligned for maximum correspondence over a comparison window as measured using one of the following sequence comparison algorithms or by manual alignment and visual inspection. Preferably, the percent identity exists over a region of the sequence that is at least about 25 amino acids in length, more preferably over a region that is 50 or 100 amino acids in length.

When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters.

A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5: 151–153 (1989). The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison, e.g., the core motor region of CENP-E. In one example, hCENP-E, XCENP-E and ustilago CENP-E were compared to other kinesin superfamily sequences using the following parameters: default gap weight (3.00), default gap length weight (0.10), and weighted end gaps. The resulting dendogram placed hCENP-E and XCENP-E in one cluster as the most closely related sequences, with ustilago CENP-E in the next most closely related cluster.

Another example of algorithm that is suitable for determining percent sequence identity (i.e., substantial similarity or identity) is the BLAST algorithm, which is described in Altschul et al., *J. Mol. Biol.* 215:403–410 (1990). Software for performing BLAST analyses is publicly available through the National Center for Biotechnology Information (http://www.ncbi.nlrn.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see. Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium (as the target sequences are generally present in excess, at $T_m$, 50% of the probes are occupied at equilibrium). Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

"High stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 λg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like."

The phrase "a sequence encoding a gene product" refers to a nucleic acid that contains sequence information, e.g., for a structural RNA such as rRNA, a tRNA, the primary amino acid sequence of a specific protein or peptide, a binding site for a transacting regulatory agent, an antisense RNA or a ribozyme. This phrase specifically encompasses degenerate codons (i.e., different codons which encode a single amino acid) of the native sequence or sequences which may be introduced to conform with codon preference in a specific host cell.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see *Fundamental Immunology* (Paul, ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

An "anti-XCENP-E" antibody is an antibody or antibody fragment that specifically binds a polypeptide encoded by the XCENP-E gene, cDNA, or a subsequence thereof.

Humanized forms of non-human antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature*, 321:522–525 (1986); Riechmann et al., *Nature*, 332:323–329 (1988); and Presta, *Curr. Op. Struct. Biol.*, 2:593–596 (1992)).

Methods for humanizing non-human antibodies are well known in the art. Generally, a humanized antibody has one or more amino acid residues introduced into it from a source which is non-human. These non-human amino acid residues are often referred to as "Import" residues, which are typically taken from an "Import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom & Winter, *J. Mol. Biol.*, 227:381 (1991); Marks et al., *J. Mol. Biol.*, 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg & Huszar, *Intern. Rev. Immunol.* 13 65–93 (1995).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an analyte. The immunoassay is characterized by the use of specific binding properties of a particular antibody to isolate, target, and/or quantify the analyte.

The phrase "specifically (or selectively) binds to an antibody" or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to XCENP-E with the amino acid sequence encoded in SEQ ID NO:1 can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "plus end-directed microtubule motor activity" refers to the activity of a motor protein such as CENP-E to power movement toward the "plus" ends of microtubules. Microtubules are conventionally referred to as having plus (fast growing) and minus ends (slow growing). For example, microtubules of the mitotic spindle have their slow growing, minus ends anchored at or near the spindle pole, and their dynamic, fast growing plus ends interacting with chromosomes and with microtubules emanating from the opposite pole.

The term "motor domain" or "core motor domain" refers to the domain of CENP-E that confers the plus end-microtubule motor activity on the protein.

"CENP-E" refers to centromere-associated protein, which is a member of the kinesin superfamily of microtubule motor proteins. CENP-E is an integral component of the kinetochore structure of the chromosome, which links the chromosome to the spindle microtubules. "XCENP-E" refers to CENP-E isolated from Xenopus. CENP-E has activity such as ATPase activity, microtubule binding activity, and plus end-directed microtubule motor activity.

"Modulators of CENP-E" refers to modulatory molecules identified using an in vitro assays for CENP-E activity (e.g., inhibitors and activators or enhancers). Such assays include ATPase activity, microtubule gliding, spindle assembly, microtubule depolymerizing activity, and metaphase arrest. Samples or assays that are treated with a at least one candidate agent at a test concentration are compared to control samples having the candidate agent at a control concentration (which can be zero), to examine the extent of modulation. Control samples are assigned a relative CENP-E activity value of 100. Modulation of CENP-E is achieved when the CENP-E activity value relative to the control is increased or decreased about at least 10%, 20%, 30%, 40%, 50%, 75%, or preferably, at least 100%.

"Biologically active" CENP-E refers to CENP-E that has at least one activity selected ATPase activity, microtubule binding activity, and plus end-directed microtubule motor activity, as tested in an ATPase assay, microtubule binding assay, or a microtubule gliding assay. "ATPase activity" refers to the ability of CENP-E to hydrolyze ATP. In a preferred embodiment, CENP-E has plus-end directed microtubule activity.

III. Isolation of the XCENP-E Gene

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.*, 22:1859–1862 (1981), using an automated synthesizer, as described in Van Devanter et. al., *Nucleic Acids Res.*, 12:6159–6168 (1984). Purification of oligonucleotides is by either native acrylamide gel electrophoresis or by anion-exchange HPLC as described in Pearson & Reanier, *J. Chrom.*, 255:137–149 (1983).

The sequence of the cloned genes and synthetic oligonucleotides can be verified after cloning using, e.g., the chain termination method for sequencing double-stranded templates of Wallace et al., *Gene*, 16:21–26, 1981.

B. Cloning Methods for the Isolation of Nucleotide Sequences Encoding XCENP-E

In general, the nucleic acid sequences encoding XCENP-E and related nucleic acid sequence homologues are cloned from cDNA and genomic DNA libraries or isolated using amplification techniques with oligonucleotide primers. For example, XCENP-E sequences can be isolated from Xenopus DNA libraries by hybridizing with a nucleic acid probe, the sequence of which can be derived from human CENP-E. XCENP-E and XCENP-E homologues that are substantially identical to XCENP-E can be isolated using XCENP-E nucleic acid probes and oligonucleotides under stringent hybridization conditions, by screening libraries. Alternatively, expression libraries can be used to clone XCENP-E and XCENP-E homologues, by detecting expressed homologues immunologically with antisera or purified antibodies made against XCENP-E that also recognize and selectively bind to the XCENP-E homologue. Finally, amplification techniques using primers can be used to amplify and isolate XCENP-E from DNA or RNA. Amplification techniques using degenerate primers can also be used to amplify and isolate XCENP-E homologues. Amplification techniques using primers can also be used to isolate a nucleic acid encoding XCENP-E. These primers can be used, e.g., to amplify a probe of several hundred nucleotides, which is then used to screen a library for full-length XCENP-E. The following primers can be used in such a manner: SEQ ID NO:5 GGGCTGCCCAGGAAGAG and SEQ ID NO:6 GACAGCATTGATCGGCG. Alternatively, the nucleic acid for XCENP-E can be directly amplified using the following primers: SEQ ID NO:7 GAGGGTTCGGCCGCTTA and SEQ ID NO:8 TCTGGGGCCATCCATGC.

Appropriate primers and probes for identifying the gene encoding CENP-E in other species such as Drosophila and fungi are generated from comparisons of the sequences provided herein (SEQ ID NOS:1 and 2). As described above, antibodies can be used to identify XCENP-E homologues. For example, antibodies made to the motor domain of XCENP-E, the tail domain of XCENP-E, or to the whole protein are useful for identifying XCENP-E homologues (see Example section, below).

To make a cDNA library, one should choose a source that is rich in the mRNA of choice, e.g., XCENP-E. For example, ovary tissue is enriched for XCENP-E mRNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25: 263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating XCENP-E nucleic acid and its homologues combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of CENP-E directly from mRNA, from cDNA, from genomic libraries or cDNA libraries. Degenerate oligonucleotides can be designed to amplify XCENP-E homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of CENP-E encoding mRNA in physiological samples, for nucleic acid sequencing, or for other purposes. Genes amplified by the PCR reaction can be purified from agarose gels and cloned into an appropriate vector.

Gene expression of CENP-E can also be analyzed by techniques known in the art, e.g., reverse transcription and amplification of mRNA, isolation of total RNA or poly A+RNA, northern blotting, dot blotting, in situ hybridization, RNase protection and the like.

Synthetic oligonucleotides can be used to construct recombinant XCENP-E genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the XCENP-E gene. The specific subsequence is then ligated into an expression vector.

The gene for Xenopus CENP-E is typically cloned into intermediate vectors before transformation into prokaryotic or eukaryotic cells for replication and/or expression. These intermediate vectors are typically prokaryote vectors or shuttle vectors.

C. Expression in Prokaryotes and Eukaryotes

To obtain high level expression of a cloned gene, such as those cDNAs encoding CENP-E, it is important to construct an expression vector that contains, at the minimum, a strong promoter to direct transcription, a ribosome binding site for translational initiation, and a transcription/translation terminator. Suitable bacterial promoters are well known in the art and described, e.g., in Sambrook et al. and Ausubel et al. Bacterial expression systems for expressing the CENP-E protein are available in, e.g., *E. coli*, Bacillus sp., and Salmonella (Palva et al., *Gene* 22:229–235 (1983); Mosbach, et al., *Nature*, 302:543–545 (1983). Kits for such expression systems are commercially available. Eukaryotic expression systems for mammalian cells, yeast, and insect cells are well known in the art and are also commercially available. The pET23D expression system (Novagen) is a preferred prokaryotic expression system.

A "Promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences which are not found in the same relationship to each other in nature. For instance, the nucleic acid is typically recombinantly produced, having two or more sequences from unrelated genes arranged to make a new functional nucleic acid.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the CENP-E encoding DNA in host cells. A typical expression cassette thus contains a promoter operably linked to the DNA sequence encoding CENP-E and signals required for efficient polyadenylation of the transcript, ribosome binding sites, and translation termination. The DNA sequence encoding the CENP-E may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, and fusion expression systems such as GST and LacZ. Epitope tags can also be added to recombinant proteins to provide convenient methods of isolation. One preferred embodiment of an epitope tag is c-myc.

Expression vectors containing regulatory elements from eukaryotic viruses are typically used in eukaryotic expression vectors, e.g., SV40 vectors, papilloma virus vectors, and vectors derived from Epstein Bar virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a bacculovirus vector in insect cells, with a CENP-E encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of CENP-E protein, which are then purified using standard techniques (see, e.g., Colley et al., *J. Biol. Chem.* 264:17619–17622 (1989); *Guide to Protein Purification, in Methods in Enzymology*, vol. 182 (Deutscher ed., 1990)). Transformation of eukaryotic and prokaryotic cells are performed according to standard techniques (see, e.g., Morrison, *J. Bact.*, 132:349–351 (1977); Clark-Curtiss & Curtiss, *Methods in Enzymology*, 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the CENP-E protein.

After the expression vector is introduced into the cells, the transfected cells are cultured under conditions favoring expression of the CENP-E protein which is recovered from the culture using standard techniques identified below.

IV. Purification of CENP-E Protein

Either naturally occurring or recombinant CENP-E can be purified for use in functional assays. Naturally occurring CENP-E is purified, e.g., from Xenopus and any other source of an XCENP-E homologue, such as Drosophila or fungi. Recombinant CENP-E is purified from any suitable expression system.

CENP-E may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra). A preferred method of purification is use of Ni-NTA agarose (Qiagen).

A number of procedures can be employed when recombinant CENP-E is being purified. For example, proteins having established molecular adhesion properties can be reversible fused to CENP-E. With the appropriate ligand, CENP-E can be selectively adsorbed to a purification column and then freed from the column in a relatively pure form. The fused protein is then removed by enzymatic activity. Finally CENP-E could be purified using immunoaffinity columns.

A. Purification of CENP-E from Recombinant Bacteria

Recombinant proteins are expressed by transformed bacteria in large amounts, typically after promoter induction; but expression can be constitutive. Bacteria are grown according to standard procedures in the art. Because CENP-E is a protein that is difficult to isolate with intact biological activity, preferably fresh bacteria cells are used for isolation of protein. Use of cells that are frozen after growth but prior to lysis typically results in negligible yields of active protein.

Proteins expressed in bacteria may form insoluble aggregates ("inclusion bodies"). Several protocols are suitable for purification of CENP-E inclusion bodies. For example, purification of inclusion bodies typically involves the extraction, separation and/or purification of inclusion bodies by disruption of bacterial cells, e.g., by incubation in a buffer of about 100–150 μg/ml lysozyme and 0.1% Nonidet P40, a non-ionic detergent. The cell suspension can be homogenized using a Polytron (Brinkman Instruments, Westbury, N.Y.). Alternatively, the cells can be sonicated on ice. Alternate methods of lysing bacteria are apparent to those of skill in the art (see, e.g., Sambrook et al., supra; Ausubel et al., supra).

The cell suspension is generally centrifuged and the pellet containing the inclusion bodies resuspended in buffer that does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties); the proteins that formed the inclusion bodies may then be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. After solubilization, the protein can be separated from other bacterial proteins by standard separation techniques.

Alternatively, it is possible to purify CENP-E from bacteria periplasm. Where CENP-E is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 MM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques For Purifying CENP-E

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

CENP-E has a known molecular weight and this knowledge can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

CENP-E can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of CENP-E

In addition to the detection of CENP-E genes and gene expression using nucleic acid hybridization technology, one can also use immunoassays to detect CENP-E. Immunoassays can be used to qualitatively or quantitatively analyze CENP-E. A general overview of the applicable technology can be found in Harlow & Lane, *Antibodies: A Laboratory Manual* (1988).

A. Antibodies to CENP-E

Methods of producing polyclonal and monoclonal antibodies that react specifically with CENP-E are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature,* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of CENP-E comprising immunogens may be used to produce antibodies specifically reactive with CENP-E. For example, recombinant XCENP-E or a antigenic fragment thereof such as the motor or tail domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice or rabbits is immunized with the protein using a standard adjuvant, such as Freund's adjuvant, and a standard immunization protocol. The animal's immune response to the immunogen preparation is monitored by taking test bleeds and determining the titer of reactivity to CENP-E. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-CENP-E proteins or even other homologous proteins from other organisms, using a competitive binding immunoassay. Specific polyclonal antisera and monoclonal antibodies will usually bind with a $K_D$ of at least about 0.1 mM, more usually at least about 1 $\mu$M, preferably at least about 0.1 $\mu$M or better, and most preferably, 0.01 $\mu$M or better.

Once CENP-E specific antibodies are available, CENP-E can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

As explained above, CENP-E expression is associated with mitosis. Thus, CENP-E provides a marker with which to examine actively dividing cells, including pathological cells such as cancers or hyperplasias. In a preferred embodiment, CENP-E is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology* (Asai, ed. 1993); *Basic and Clinical Immunology* (Stites & Terr, eds., 7th ed. 1991). Immunological binding assays (or immunoassays) typically utilize a "capture agent" to specifically bind to and often immobilize the analyte (in this case the CENP-E or antigenic subsequence thereof). The capture agent is a moiety that specifically binds to the analyte. The antibody (anti-CENP-E) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled CENP-E polypeptide or a labeled anti-CENP-E antibody. Alternatively, the labeling agent may be a third moiety, such as another antibody, that specifically binds to the antibody/CENP-E complex.

In a preferred embodiment, the labeling agent is a second CENP-E bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see generally Kronval, et al., *J. Immunol.*, 111: 1401–1406 (1973); Akerstrom, et al., *J. Immunol.*, 135: 2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting CENP-E in samples may be either competitive or noncompetitive. Noncompetitive immunoassays are assays in which the amount of captured analyte (in this case the protein) is directly measured. In one preferred "sandwich" assay, for example, the capture agent (anti-CENP-E antibodies) can be bound directly to a solid substrate on which they are immobilized. These immobilized antibodies then capture CENP-E present in the test sample. CENP-E is thus immobilized is then bound by a labeling agent, such as a second CENP-E antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Competitive Assay Formats

In competitive assays, the amount of CENP-E (analyte) present in the sample is measured indirectly by measuring the amount of an added (exogenous) analyte (i.e the CENP-E) displaced (or competed away) from a capture agent (anti-CENP-E antibody) by the analyte present in the sample. In one competitive assay, a known amount of, in this case, the CENP-E is added to the sample and the sample is then contacted with a capture agent, in this case an antibody that specifically binds to the CENP-E. The amount of CENP-E bound to the antibody is inversely proportional to the concentration of CENP-E present in the sample. In a particularly preferred embodiment, the antibody is immobilized on a solid substrate. The amount of the CENP-E bound to the antibody may be determined either by measuring the amount of CENP-E present in an CENP-E/antibody complex, or alternatively by measuring the amount of remaining uncomplexed protein. The amount of CENP-E may be detected by providing a labeled CENP-E molecule.

A hapten inhibition assay is another preferred competitive assay. In this assay a known analyte, in this case CENP-E, is immobilized on a solid substrate. A known amount of anti-CENP-E antibody is added to the sample, and the sample is then contacted with the immobilized CENP-E. The amount of anti-CENP-E antibody bound to the immobilized CENP-E is inversely proportional to the amount of CENP-E present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for crossreactivity determinations. For example, a protein partially encoded by SEQ ID NO:1 can be immobilized to a solid support. Proteins are added to the assay that compete with the binding of the antisera to the immobilized antigen. The ability of the above proteins to compete with the binding of the antisera to the immobilized protein is compared to CENP-E encoded by SEQ ID NO:1. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorption with the considered proteins, e.g., distantly related homologues.

The immunoabsorbed and pooled antisera are then used in a competitive binding immunoassay as described above to compare a second protein, thought to be perhaps the protein of this invention, to the immunogen protein (i.e., CENP-E of SEQ ID NO:1). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein partially encoded by SEQ ID NO:1 that is required to inhibit 50% of binding, then the second protein is said to specifically bind to the polyclonal antibodies generated to an CENP-E immunogen.

Other Assay Formats

Western blot (immunoblot) analysis is used to detect and quantify the presence of CENP-E in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the CENP-E. The anti-CENP-E antibodies specifically bind to the CENP-E on the solid support. These antibodies may be directly labeled or alternatively may be subsequently detected using labeled antibodies (e.g., labeled sheep anti-mouse antibodies) that specifically bind to the anti-CENP-E antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e. g., Dynabeads™), fluorescent dyes (e.g., fluorescein isothiocyanate, Texas red, rhodamine, and the like), radiolabels (e.g., $^3$H, $^{125}$I, $_{35}$C, $^{14}$C, or $^{32}$P), ezymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of CENP-E

CENP-E is a plus end-directed microtubule motor that is required for mitosis. The present invention provides for the first time biologically active CENP-E. The activity of CENP-E can be assessed using a variety of in vitro assays, e.g., microtubule gliding assays (see Example II) or ATPase assays (Kodama et al., *J. Biochem.* 99: 1465–1472 (1986); Stewart et al., *Proc. Nat'l Acad. Sci. USA* 90: 5209–5213 (1993). Microtubule depolymerization assays can also be used to examine CENP-E activity (Lombillo et al., *J. Cell Biol.* 128:107–115 (1995)).

In addition, CENP-E activity can be examined by comparing antibody depletion of CENP-E or inhibition of CENP-E in vitro using cultured cells or egg extracts. Samples that have been depleted or inhibited are compared to control samples that are not inhibited/depleted or that have biologically CENP-E added back to the sample. Characteristics such as spindle assembly and metaphase arrest are used to compare the effect of CENP-E inhibition or depletion.

Such assays can be used to test for the activity of CENP-E isolated from endogenous sources or recombinant sources. Furthermore, such assays can be used to test for modulators of CENP-E. Because the plus end-directed microtubule motor activity of CENP-E is essential for mitosis, inhibition of CENP-E can be used to control cell proliferation.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, or ionic (electrostatic) interactions and typically include at least an amine, carbonyl, hydroxyl, sulfonyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In an embodiment provided herein, the candidate bioactive agents are proteins. The protein may be made up of naturally occurring amino acids and peptide bonds, or synthetic peptidomimetic structures. For example, homophenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In another embodiment, the candidate bioactive agents are naturally occurring proteins or fragments of naturally occurring proteins. Thus, for example, cellular extracts containing proteins, or random or directed digests of proteinaceous cellular extracts, may be used. In one embodiment, the libraries are of bacterial, fungal, viral, and mammalian proteins, with the latter being preferred, and human proteins being especially preferred.

In one embodiment, the candidate agents are peptides of from about 5 to about 30 amino acids, with from about 5 to about 20 amino acids being preferred, and from about 7 to about 15 being particularly preferred. The peptides may be digests of naturally occurring proteins as is outlined above, or random peptides. By randomized or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In another embodiment, the candidate agents are nucleic acids. By nucleic acid or "oligonucleotide" or grammatical equivalents herein means at least two nucleotides covalendy linked together. A nucleic acid of the present invention will generally contain phosphodiester bonds, although in some cases, as outlined below, nucleic acid analogs are included that may have alternate backbones, comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984), Letsinger et al., *J. Am.*

Chem. Soc. 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc.* 114:1895 (1992); Meier et al., *Chem. Int. Ed. Engl.* 31:1008 (1992); Nielsen, *Nature*, 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowski et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, *Carbohydrate Modifications in Antisense Research,* Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al., *Chem. Soc. Rev.* (1995) pp. 169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine, hypoxanthine, isocytosine, isoguanine, etc.

As described above generally for proteins, nucleic acid candidate agents may be naturally occurring nucleic acids, random nucleic acids, or biased random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate agent is a small molecule. The small molecule is preferably 4 kilodaltons (kd) or less. In another embodiment, the compound is less than 3 kd, 2 kd or 1 kd. In another embodiment the compound is less than 800 daltons (D), 500 D, 300 D or 200 D. Alternatively, the small molecule is about 75 D to 100 D, or alternatively, 100 D to about 200 D.

The modulators that are identified herein may be useful as lead compounds for therapeutics, bioagricultural compounds, or diagnostics. A therapeutic as used herein refers to a compound which is believed to be capable of modulating CENP-E in vivo which can have treatment application in both human and animal disease. Modulation of CENP-E would be desirable in a number of conditions including but not limited to: abnormal stimulation of endothelial cells (e.g., atherosclerosis), solid and hematopoetic tumors and tumor metastasis, benign tumors, for example, hemangiomas, acoustic neuromas, neurofibromas, vascular malfunctions, abnormal wound healing, inflammatory and immune disorders such as Rheumatoid Arthritis, Bechet's disease, gout or gouty arthritis, abnormal angiogenesis accompanying: rheumatoid arthritis, psoriasis, diabetic retinopathy, and other ocular angiogenic diseases such as, macular degeneration, corneal graft rejection, corneal overgrowth, glaucoma, Osler Webber syndrome, cardiovascular diseases such as hypertension, cardiac ischemia and systolic and diastolic dysfunction and fungal diseases such as aspergifiosis, candidiasis and topical fungal diseases such as tinea pedis.

A bioagricultural compound as used herein refers to a chemical or biological compound that has utility in agriculture and functions to foster food or fiber crop protection or yield improvement. For example, one such compound may serve as a herbicide to selectively control weeds, as a fungicide to control the spreading of plant diseases, as an insecticide to ward off and destroy insect and mite pests. In addition, one such compound may demonstrate utility in seed treatment to improve the growth environment of a germinating seed, seedling or young plant as a plant regulator or activator.

A diagnostic as used herein is a compound that assists in the identification and characterization of a health or disease state in humans or other animals. The diagnostic can be used in standard assays as is known in the art.

The modulators can be applied to generally any cell type wherein CENP-E modulation is desired, i.e., eukaryotic, single celled and multicelled organisms, plant and animal, vertebrate, invertebrate and mammalian.

Modulators of CENP-E are tested using biologically active CENP-E, preferably biologically active XCENP-E. Modulation is tested using one of the in vitro assays described above, e.g., ATPase, microtubule binding and/or gliding, spindle assembly, and metaphase arrest. It is understood that any of the assays can be repeated or different types of assays can be used on the same candidate agent to further characterize the candidate agent as a CENP-E modulator. In particular, where more than one candidate agent is used, the assay can be repeated using individual candidate agents. Moreover, where a candidate agent is a lead compound, further assays can be performed to optimize results until it is established whether that compound or one similar thereto has the desired effect.

As described above, CENP-E is also a useful diagnostic tool in vitro for determining when a cell is entering mitosis. Reversible inhibitors of CENP-E can be used to synchronize cells in culture. Fungal homologues of XCENP-E also provide a diagnostic tool for identifying fungal infections.

The present invention also provides for kits for screening for modulators of CENP-E. Such kits can be prepared from readily available materials and reagents. For example, such kits can comprise any one or more of the following materials: biologically active CENP-E, reaction tubes, and instructions for testing CENP-E activity. Preferably, the kit contains biologically active XCENP-E. A wide variety of kits and components can be prepared according to the present invention, depending upon the intended user of the kit and the particular needs of the user. For example, the kit can be tailored for ATPase assays or microtubule gliding assays.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Methods

A. Isolation of XCENP-E cDNA and DNA Constructs

Fragments spanning nucleotides 1–1707 and 6376–8080 of human CENP-E cDNA (Yen, et al., *Nature* 359:536–539 (1992)) were used to screen a λgt1O adult Xenopus ovary cDNA library (Rebagliati, et al., *Cell* 42:769–777 (1985)), hybridizing at 42° C. according to Church & Gilbert (Church, et al., *Proc. Natl. Acad. Sci. USA* 81:1991–1995 (1984)). cDNA clones hybridizing to both probes were isolated and used in combination to isolate overlapping cDNA clones spanning the intervening region. The sequence of both cDNA strands was determined by a combination of automated cycle sequencing (Applied Biosystems, Perkin Elmer) and manual sequencing using Sequenase version 2.0 (USB).

Overlapping regions of the various cDNA clones were often not absolutely identical, but displayed single base differences at multiple positions. One clone encoding the N-terminal region of the rod domain contained 27 additional nucleotides relative to one other clone spanning that region. Single base differences between cDNA clones were attributed to polymorphisms present in the outbred psuedotetraploid source material used to construct the cDNA library. The 27 nucleotide relative insertion may be a polymorphism, or may represent an alternatively spliced XCENP-E isoform. Overlapping sequence was compiled using MacVector software (Kodak Scientific Imaging Systems, Rochester, N.Y.).

B. Expression and Purification of XCENP-E Motor Domain

Recombinant CENP-E was prepared in order to test its activity in a microtubule gliding assay. The recombinant XCENP-E was prepared as a fusion protein inducible by IPTG, with a c-myc epitope tag.

First, an XCENP-E was cloned into an expression plasmid. The 5' untranslated region of XCENP-E was removed by PCR using two primers: SEQ ID NO:9 CATATGAC-CATGGCCGAGGGAGATGCAG and SEQ ID NO:10 GTCAGGTCAGCAACATACACG. These primers were used to amplify the 5' end of the X-CENP-E cDNA and introduce NdeI and NcoI sites adjacent to and at the start codon, respectively. This PCR product was subcloned into pCRII (InVitrogen) and then joined at the NruI site with a portion of the XCENP-E cDNA, to reconstruct a motor domain encoding cDNA with an altered start codon.

An NcoI-XhoI fragment spanning nucleotides 143–1939 was excised from the reconstructed cDNA fragment and ligated into NcoI/XhoI cut pET23d (Novagen) to yield pET23dXCE. This plasmid was digested with BsrGI and XhoI, blunted with Klenow, and a Klenow blunted 60 bp HincII-EcoRI fragment from pBSKS+myc (gift from S. Michealis) was ligated to the digested pET23dXCE backbone in the presence of BsrGI to bias orientation of the insert. The resulting plasmid, pET23dXCEMycHis, encodes amino acids 1–473 of XCENP-E linked at the C-terminus to the following sequence: SEQ ID NO:11 TVSISLGDLTM EOKLISEEDLNFEHHHHHH. The c-myc epitope is underlined.

This plasmid was transformed into *E. coli* strain BL21 (DE3) pLysS. A culture inoculated with a single colony was gown at 37° C. in a modified LB medium (10 g bactotryptone, 5 g yeast extract, 5 g NaCl, 2 g MgSO$_4$, 1 g casaminoacids per liter, and 200 mg ampicillin per liter) to OD 600 of ~1. The cultures were allowed to cool to room temperature and expression of fusion protein was induced with 0.5 mM IPTG at room temperature. After induction, the cells were used immediately to prepare fusion protein. Cells that were pelleted and stored at low temperatures prior to protein isolation gave low to no yield of active protein, due to CENP-E sensitivity to denaturation.

Cells were harvested 4 hours after induction, immediately resuspended in lysis buffer (50 mM Tris-HCl pH 7.5, 50 mM NaCl, 1 mM PMSF, 0.1 mM ATP), and lysed by 3 passages through a trench press. Insoluble debris was removed by a centrifugation at 35,000 rpm in Sorvall T647.5 rotor for 40 minutes at 4° C. Soluble protein in the supernatant was bound in batch to 0.5 ml of NTI-agarose resin (Qiagen) for 15 minutes at 4° C. The resin was placed in a column, washed with 5 ml of the lysis buffer supplemented with 20 mM Imidazole. XCENP-E fusion protein recovered by elution in lysis buffer containing 100 mM imidazole and 1 mM DTT. A typical yield was ~2 mg of soluble XCENP-E protein from 1 liter of bacterial culture. Freshly prepared protein was used to assay motility. Incubation of bacterially expressed XCENP-E motor protein for longer than 24 hours at 4° C. led to loss of motility.

C. Fusion Protein Expression, Antibody Production, and Immunoblotting

The tail and rod regions (see FIG. 1) of XCENP-E were used to make antibodies to CENP-E. Antigens for α-XCENP-E$_{TAIL}$ (aa 2396–2954) and α-XCENP-E$_{ROD}$ (aa 826–1106) were produced in *E. coli* strain BL21 (DE3) pLysS as hexahistidine fusion proteins using the pRSETB expression plasmid (InVitrogen). Following induction with IPTG for 4–16 hours, bacteria were pelleted, washed and lysed by rapid freeze thaw followed by sonication. Inclusion bodies containing the fusion proteins were purified and solubilized in 8M urea, 0.1 M sodium phosphate pH 8.0.

α-XCENP-E$_{ROD}$ fusion protein was further purified over Ni-NTA agarose (Qiagen) according to the manufacturer's instructions. α-XCENP-E$_{TAIL}$ protein was isolated from preparative SDS-PAGE gels as described in (Harlow, et al., *Antibodies, A Laboratory Manua*: Cold Spring Harbor Laboratory) (1988)). These antigens were used to raise polyclonal antibodies in rabbits.

For affinity purification, antigen was coupled to cyanogen bromide activated Sepharose (Pharmacia) according to the manufacturers instructions. Antibodies were purified (Harlow, et al., *Antibodies, A Laboratory Manual* (1988)), eluting with 0.2 M glycine pH 2.5. Antibodies were dialyzed into 10 mM K-HEPES pH 7.8, 100 mM KCl, 1 mM MgCl$_2$ and concentrated using prerinsed centricon spin concentrators (Amicon, Beverly, Mass.) or Nanospin filter concentrators (Gelman Sciences, Ann Arbor, Mich.).

For immunoblots, cytoplasmic extract prepared from metaphase H arrested Xenopus eggs (Murray, in *Methods in Cell Biology*, pp. 581–605 (Kay & Peng, eds., (1991)) was resolved on a 4% polyacrylamide gel (~50 μg/lane), transferred to nitrocellulose and lanes individually probed with affinity purified α-XCENP-$E_{TAIL}$ or α-XCENP-$E_{ROD}$.

For localization of XCENP-E in cultured Xenopus XTC cells, asynchronous cultures of XTC cells were fixed in methanol and simultaneously stained with mouse monoclonal anti-α-tubulin antibody and affinity purified rabbit α-XCENP-$E_{TAIL}$ antibody. Chromatin was visualized by staining with DAPI. Selected cells at progressive stages of the cell cycle were examined on the blot: interphase, prophase, prometaphase, metaphase, anaphase, and telophase. Similar staining was observed using (x-XCENP-$E_{ROD}$ antibody.

Immunoblots were prepared as follows: proteins resolved by SDS-PAGE, transferred to nitrocellulose, blocked with TBS 5% nonfat dried milk (NFDM), and probed with 2 μg/ml affinity purified antibody overnight in TBS containing 0.05% Tween (TBST) containing 5% NFDM. Primary antibody was visualized using $^{125}$I-Protein A (Amersham) followed by autoradiography. Occasionally, instead of $^{125}$I-protein A, alkaline phosphatase conjugated goat anti-rabbit secondary antibody (Promega) was used according to the manufacturers instructions. Quantitative phosphoimaging was performed using a Molecular Dynamics model 445 SI phophorimager.

D. Spindle Assembly in vitro

CSF-arrested extract is an Xenopus egg extract that is arrested in metaphase using cytostatic factor. CSF-arrested extract was prepared from Xenopus eggs essentially as described in Murray, in Methods in Cell Biology, pp. 581–605 (Kay & Peng, eds. 1991); Sawin, et al., J. Cell Biol. 112:925–940 (1991)). 10 mg/ml rhodamine labelled bovine brain tubulin (Hyman, et al., in Methods in Enzymology, pp. 478–485(Vallee, ed., 1992)) was added at a 1 μl/300 μl of extract.

Localization of XCENP-E was examined on mitotic spindles assembled in vitro. Tubulin, DAPI-stained chromatin, and α-XCENP-$E_{TAIL}$ staining was examined. Metaphase spindles were assembled in vitro by cycling CSF-arrested Xenopus egg extract containing Xenopus sperm chromatin through interphase and arresting at the following metaphase as described (Sawin, et al., J. Cell Biol. 112:925–940 (1991)). Rhodamine labelled tubulin was added to the extracts to visualize tubulin containing structures. Spindles were sedimented onto coverslips and stained with affinity purified α-XCENP-$E_{TAIL}$ antibody, followed by FITC-conjugated secondary antibody and DAPI.

For immunodepletion of extract, 100 μg of affinity purified α-XCENP-E antibody or non-immune rabbit IgG (Calbiochem, San Diego, Calif.) was bound to 30 μl slurry of protein A Affiprep beads (BioRad, Hercules, Calif.) for 1 hour at 4° C. in CSF-XB (Murray, 1991). Beads were sedimented, unbound antibody removed, and serially washed with CSF-XB, CSF-XB containing 0.5 M NaCl, and CSF-XB containing leupeptin, pepstatin A, and chymostatic (10 μg/ml each), and cytochalasin B 10 μg/ml. 100 μl of CSF extract was added to the beads and incubated rocking for 1 hour at 4° C. After sedimenting beads, depleted extract was removed and stored on ice until use.

Demembranated sperm prepared as described (Newmeyer, et al., in Methods in Cell Biology, pp. 607–634 (Kay & Peng, eds. (1991)) were added to a portion of the extract at 1–2×10$^5$/ml, and exit from metaphase arrest induced at room temperature by addition of $CaCl_2$ to 0.6–0.8 mM final concentration. Extracts were periodically monitored by fluorescence microscopic examination of 1 μl aliquots squashed under a coverslip (Murray, in Methods in Cell Biology, pp. 581–605 (Kay & Peng, eds., 1991)). At 80 minutes following exit from metaphase one half volume of the appropriate extract was added and the reaction incubated for an additional 80–120 minutes.

M-phase structures accumulating in extracts were scored at 160–200 minutes total elapsed time. Both mock depleted and XCENP-E depleted extracts frequently failed to exit interphase, or failed to remain arrested at the second metaphase, probably as a consequence of experimental manipulation. Immunoprecipitates were washed 3 times with CSF-XB containing protease inhibitors and 0.1% Triton X-100 and examined by SDS-PAGE and Coomassie staining.

For Coomassie staining and α-XCENP-$E_{ROD}$ blot of α-XCENP-E immunoprecipitates, immunoprecipitates were prepared from CSF-arrested extract (~10 mg total protein) using affinity purified α-XCENP-$E_{TAIL}$ antibody, affinity purified (α-XCENP-$E_{ROD}$ antibody, or non-immune rabbit IgG. Immunoprecipitates were gently washed three times with TBS containing 0.1% Triton-X100. 80% of each precipitate was resolved by SDS-PAGE on a 5–15% gel and proteins visualized by staining with Coomassie brilliant blue.

For antibody addition experiments, purified anti-XCENP-E antibody or non-immune rabbit IgG (Calbiochem) at 10 mg/ml was added to CSF-arrested extract at a 1:20 dilution, followed by demembranated sperm nuclei and $CaCl_2$. 80 minutes later, when a half volume of CSF arrested extract was added, a proportional amount of the appropriate antibody was added as well.

Representative structures formed in the presence of 0.5 mg/ml rabbit IgG and in the absence of added antibody, and in the presence of 0.5 mg/ml α-XCENP-$E_{TAIL}$ antibody were examined. Rabbit IgG and α-XCENP-$E_{TAIL}$ (both at 10 mg/ml) were added to CSF-arrested metaphase Xenopus egg extract at a 1:20 dilution along with Xenopus sperm. Extracts were then cycled through interphase. At 80 minutes into interphase (prophase) a half volume of metaphase arrested extract containing 0.5 mg/ml of the appropriate antibody was added. 80 minutes later structures were scored and images collected.

Quantitation of structures formed in extract containing no antibody (n=138), extract containing 0.5 mg/ml non-immune rabbit IgG (n=132), and extract containing 0.5 mg/ml α-XCENP-$E_{TAIL}$ (n=114) at 80 minutes after exit from interphase were examined. Structures present in the respective extracts were examined and scored as belonging to one of four categories: bipolar spindles with chromatin aligned at the metaphase plate; bipolar spindles with misaligned chromosomes; monopolar spindles, including radial asters, half spindles and chromosomes associated with microtubules with indeterminant organization; and or other, including multipolar structures and groups of chromosomes apparently unassociated with microtubules.

E. Immunofluorescence Microscopy

Extract containing mitotic spindles assembled in vitro was diluted 30–50 fold in BRB80 (80 mM KPIPES, 6 mM $MgCl_2$, 1 mM EGTA) containing 0.5% Triton X-100 and 30% glycerol. Spindles were sedimented at room temperature onto a coverslip through a 3 ml cushion of BRB80 containing 0.5% Triton X-100 and 40% glycerol at 7000 rpm in a Sorvall HS4 rotor. Coverslips were fixed in −20° C. methanol, rehydrated in TBS-Tx (150 mM NaCl, 20 mM Tris pH 7.6, 0.1% Triton X-100), blocked for 1 hour with 1% BSA in TBS-Tx and probed with 5 μg/ml affinity purified antibody in 1% BSA in TBS-Tx. After washing with TBS-Tx, primary antibody was visualized using by FITC-conjugated secondary goat anti-rabbit antibody (Cappel).

Xenopus XTC cells cultured on coverslips in 60% L15 medium containing 10% fetal calf serum at room temperature in ambient atmosphere were rinsed in TBS, fixed in −20° C. methanol and stained with affinity purified antibody as described above. Monoclonal anti-alpha tubulin antibody DM1A (Sigma) was used at a dilution of 1:1000 to stain microtubules.

Fluorescent images were collected using a Princeton Instruments cooled CCD mounted on a Zeiss Axioplan microscope controlled by Metamorph software (Universal Imaging, West Chester, Pa.). Image processing was performed using both Metamorph and Adobe Photoshop software.

F. Preparation of Polarity Marked Microtubules and Motility Assay

Taxol stabilized microtubule seeds brightly labelled with rhodamine were prepared by incubating a 1:1 ratio of rhodamine labelled bovine brain tubulin (Hyman, et al., In *Methods in Enzymology*, pp. 478–485 (Vallee, ed., 1992)) with unlabelled bovine brain tubulin at a final tubulin concentration of 2.5 mg/ml in PEM80 (80 mM Pipes pH 6.9, 1 mM EGTA, 1 mM $MgCl_2$) containing 10% glycerol, 1 $\mu$M taxol, 1 mM GTP at 37° C. for 15 minutes. This mixture was then diluted with 2.75 volumes of warm PEM80 containing 20 $\mu$M taxol and 2 mM GTP, and sheared by 5 passes through a Hamilton syringe.

Dimly rhodamine-labelled extensions were grown from the brightly labelled seeds in PEM80 containing 1 mM GTP and 1.5 mg/ml tubulin cocktail consisting of a mixture of N-ethyl maleimide modified tubulin (Hyman, et al., in *Methods in Enymology*, pp. 478–485 (Vallee, ed., 1992)), unlabelled tubulin and rhodamine labelled tubulin at a ratio of 0.1/0.52/0.38 for 30 minutes at 37° C. The resulting suspension of polarity marked microtubules was diluted with PEM80 containing 10 $\mu$M taxol and used to test motility.

25 $\mu$l flow chambers prepared from cover slips sealed with an Apiezon grease, were preadsorbed with a 1:10 diluted mouse ascities fluid containing anti-myc monoclonal antibody 9EI0 (Evans, et al., *Mol. Cell. Biol.* 5:3610–3616 (1985)), washed with 50 $\mu$l PEM80, incubated with XCENP-E motor protein diluted to 0.1 mg/ml, and unbound protein removed by rinsing with 50 $\mu$l of PEM80. A microtubule/ATP mix consisting polarity marked microtubules in PEM80 containing 10 $\mu$M taxol, 2 mM MgATP, and an oxygen scavenging system (0.1 mg/ml catalase, 0.03 mg/ml glucose oxidase, 10 mM glucose, 0.1% β-mercaptoethanol (Kishino, et al., *Nature* 33:74–76 (1989)) was then flowed into the chamber.

Movement of microtubules was monitored at room temperature on a Zeiss Axioplan fluorescence microscope fitted with 63×Plan-Apochromat oil immersion objective, and a Princeton instruments cooled CCD. Automated time-lapse image acquisition and data analysis was performed using the MetaMorph software package (Universal Imaging, West Chester, Pa.).

Example I

Identification of Xenopus CENP-E

To investigate the role of CENP-E in mitotic spindle formation in vitro using extracts of Xenopus eggs used low stringency hybridization followed by library rescreening was used to clone the Xenopus homologue of CENP-E. This clone was subsequently used to raise antibodies suitable for immunodepletion and antibody addition studies. The nucleotide sequence (SEQ ID NO:2) encodes a protein of 2954 amino acids with a predicted molecular mass of 340 kDa (SEQ ID NO:1, FIG. 1C). The predicted structure of Xenopus CENP-E (XCENP-E) is similar to human CENP-E (hCENP-E), consisting of a 500 amino acid globular amino-terminal domain containing a kinesin-like microtubule motor domain linked to a globular tail domain by a region predicted to form a long, discontinuous α-helical coiled coil (Lupas, et al., *Science* 252, 1162–1164 (1991); Berger, et al., *Proc. Natl. Acad. Sci. USA* 92:8259–8263 (1995)) (FIG. 1A). Within the core of the motor domain (residues 1–324) XCENP-E and hCENP-E share 74% identity, significantly greater than that shared between XCENP-E and its nearest phylogenetic (evolutionary) neighbors (Moore, et al., *Bioessays* 18:207–219 (1996)). Outside the amino-terminal domain lie three additional regions which share greater than 25 % identity with human CENP-E, but not with other kinesin-like proteins (FIG. 1). On the basis of these regions of identity and its large predicted size, the conclusion was made that XCENP-E is the Xenopus homologue of human CENP-E.

Example II

XCENP-E is a Plus End-Directed Microtubule Motor

Both human and Xenopus CENP-E are localized to the centromeres of mitotic chromosomes throughout all phases of chromosome movement. This localization places CENP-E in a position to mediate attachment of chromosomes to microtubules, movement of chromosomes during congression, and movement of chromosomes toward the spindle poles during anaphase A.

To test directly if CENP-E is a microtubule motor and to determine the directionality of CENP-E movement, the amino-terminal 473 amino acids of XCENP-E, containing the kinesin-like motor domain, was fused at the C-terminus to 31 amino acids containing an 9 amino acid c-myc epitope tag followed by a hexahistidine tag (see FIG. 2A, and FIG. 1C, amino-terminal boxed region),.

Figure 2A:
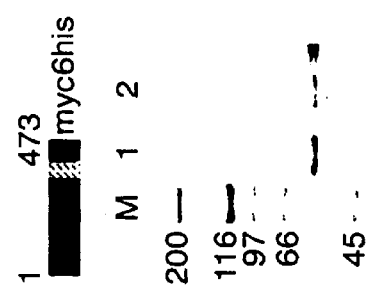
FIG. 2A–B: XCENP-E is a Plus End-Directed Microtubule Motor
Figure 2B:
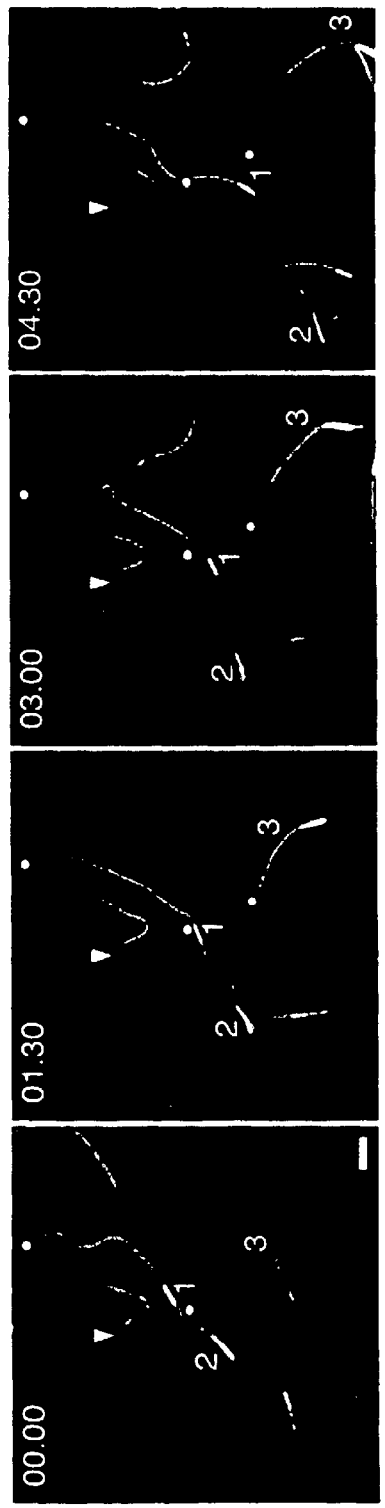

This protein was produced in *E. coli*, and purified over nickel-agarose, yielding the expected 57 kDa polypeptide as the major product (FIG. 2A, lane 1). Immunoblotting with a α-myc monoclonal antibody (9E1O) (Evans, et al., *Mol. Cell. Biol.* 5:3610–3616 (1985)) confirmed the 57 kDa protein as the XCENP-E fusion protein (FIG. 2B, lane 2, arrowheads).

The XCENP-E fusion protein was tethered to a glass coverslip using the a-myc antibody and gliding of polarity marked microtubules containing brightly fluorescent rhodamine labelled seeds near their minus ends (Howard, et al., in *Motility Assays for Motor Proteins*, pp. 105–113 (Scholey, ed., 1993)) was recorded by time-lapse digital fluorescence microscopy. Representative time points demonstrating three examples of plus end-directed movement are presented in FIG. 2B. Microtubules moved at a velocity of 5.1 $\mu$M/min±1.7 (n=49) with brightly fluorescent seeds leading, indicating that the immobilized XCENP-E fusion protein was moving toward microtubule plus ends. No movement was observed in the absence of fusion protein. When assayed in the absence of α-myc antibody the XCENP-E fusion protein also supported microtubule gliding, albeit less robustly.

This experiment demonstrates that CENP-E has plus-ended microtubule motor activity. Furthermore, by perturbing CENP-E function in Xenopus egg extracts, as shown below in Examples III–V, it was shown that congression in vitro requires a kinetochore-associated microtubule motor. This result contrasts with a prevailing model describing mitotic spindle formation in Xenopus egg extracts in vitro (Vemos, et al., *Trends in Cell Biol.* 5:297–301 (1995); Heald, et al., *Nature* 382, 420–5 (1996); Hyman, et al., *Cell* 84:401–410 (1996)). Both bipolar spindles with misaligned chromosomes and monopolar structures were observed when XCENP-E, a kinetochore-specific protein, was removed, or when XCENP-E function is impaired by addition of α-XCENP-E antibody (see Examples III–V below). These findings indicate that during normal mitotic spindle formation, CENP-E plays an essential role in mitotic spindle assembly and in prometaphase chromosome movements that result in metaphase chromosome alignment, via its activity as a plus-end directed microtubule motor activity.

Example III

XCENP-E Associates with Xenopus Centromeres in vivo and in vitro

To verify that Xenopus CENP-E exhibits a cell cycle-dependent kinetochore association, polyclonal antibodies were raised against two recombinant antigens, one spanning the tail and C-terminal portion of the rod (α-XCENP-$E_{TAIL}$, FIG. 1B) and the other corresponding to a portion of the N-terminus of the rod domain (α-XCENP-$E_{ROD}$; FIG. 1B).

Immunoblotting of Xenopus egg extract reveals that the α-XCENP-$E_{TAIL}$ antibody specifically recognizes XCENP-E as a single band of greater than 300 kDa. The α-XCENP-EROD antibody specifically recognizes XCENP-E and another protein of slightly lower molecular weight that may be a distinct isoform of XCENP-E lacking the tail domain, or XCENP-E that has lost its tail domain as a result of partial proteolysis.

Immunostaining of cultured Xenopus XTC cells using α-XCENP-$E_{TAIL}$ antibody revealed patterns of cell cycle-dependent localization similar to that observed for mammalian CENP-E (Yen, et al., *Nature* 359:536–539 (1992); Brown, et al., *J. Cell Sci.* 109:961–969 (1996)) with the exception that during interphase XCENP-E was localized to the nucleus, consistent with the presence of a nuclear localization signal (Boulikas, et al., *Gene Express.* 3:193–227 1993)) at the C-terminal end of the rod domain (FIG. 1A, NLS, and 1C underlined sequence, RKKTK). Nuclear staining intensity was variable from cell to cell, probably reflecting different levels of XCENP-E accumulation, as observed for cytoplasmic CENP-E staining of interphase human cells (Yen, et al., *Nature* 359:536–539 (1992); Brown, et al., *J. Cell. Biol.* 125:1303:1312 (1994)).

Early in prometaphase XCENP-E localizes to discrete spots associated with condensed mitotic chromosomes. During metaphase and early anaphase, XCENP-E remains in discrete foci on chromosomes, and is also apparent at the spindle poles. XCENP-E is found at the spindle midzone during late anaphase and telophase. α-XCENP-$E_{TAIL}$ immunostaining of metaphase spindles assembled using cytostatic factor (CSF)-arrested Xenopus egg extracts cycled through interphase (Murray, in *Methods in Cell Biology*, pp. 581–605 (Kay & Peng, eds. 1991); Sawin, et al., *J. Cell Biol.* 112:925–940 (1991)) revealed that XCENP-E was also associated with kinetochores assembled in vitro. Similar patterns of staining were observed in XTC cells and on spindles assembled in vitro using α-XCENP-$E_{ROD}$ antibody.

Example IV

XCENP-E is Required for Congression

To determine the aspect(s) of mitosis for which XCENP-E is required, α-XCENP-$E_{TAIL}$ antibody (made to the tail domain of XCENP-E0 was used to deplete XCENP-E from Xenopus egg extracts arrested in metaphase (CSF-extract). Immunoblotting of control and XCENP-E depleted CSF-extracts revealed that greater than 95% of XCENP-E could be removed by immunodepletion with this antibody. Unrelated antigens, such as XNuMA (Merdes, et al., *Cell* 87:447–458 (1996)), were unaffected by depletion of XCENP-E.

To examine the effects of immunodepletion on spindle assembly and chromosome movement, demembranated Xenopus sperm nuclei were added to undepleted, mock depleted and XCENP-E depleted CSF-extracts. Extracts were released from CSF-imposed metaphase arrest by addition of calcium and allowed to cycle through interphase and into the subsequent M-phase, whereupon an additional aliquot of the appropriate uncycled, metaphase-arrested XCENP-E depleted, mock depleted or undepleted extract was added to re-impose a metaphase arrest, thus allowing the accumulation of M-phase structures.

While mock depleted and undepleted extracts yielded predominantly bipolar spindles with chromosomes aligned at the metaphase plate, depletion of XCENP-E produced a five-fold increase in the number of bipolar spindles with misaligned chromosomes, as well as smaller increase in the percentage of monopolar structures, including radial asters, half spindles, and chromosomes associated with microtubules with indeterminate organization. Extended incubation failed to alter the proportion of bipolar spindles with properly aligned chromosomes. This finding, and the presence of chromosomes resembling non-disjoined metaphase sister chromatids on structures formed in the absence of XCENP-E indicates that depletion of XCENP-E prevents congression of chromosomes to the metaphase plate despite apparently normal spindle assembly and chromosome attachment.

Three independent experiments revealed in every case a decrease in the percentage of metaphase spindles accompanied by an increased percentage of bipolar/misaligned and monopolar structures, although the distribution of the aberrant structures between the monopolar and bipolar/misaligned classes was variable. Failure of XCENP-E depletion to totally prevent the appearance of bipolar spindles with properly aligned chromosomes could be due to residual XCENP-E (below detection limit), may reflect the actions of other motor proteins functioning in partial redundancy with XCENP-E, or may simply reflect that proportion of spindles in which the chromosomes were already sufficiently aligned. These data indicate that XCENP-E, or a complex containing XCENP-E, is required for chromosome congression.

To test the possibility that a multiprotein complex had been removed, the proteins immunodepleted by α-XCENP-$E_{TAIL}$ were compared with those precipitated by α-XCENP-$E_{ROD}$ antibody. Examination of the proteins immiunodepleted by α-XCENP-$E_{TAIL}$ revealed the presence of multiple bands. This result was not surprising, given that XCENP-E is relatively low in abundance compared to other spindle proteins such as NuMA (8–14 μg/ml (Merdes, et al., *Cell* 87:447–458 (1996)), XKCM1 (10 μg/ml), and Xklp2 (16 μg/ml, (Boleti, et al., *J. Cell. Biol.* 125:1303–1312).

Immunoprecipitates prepared with α-XCENP-$E_{ROD}$ antibody also contained multiple proteins, only two of which were obviously held in common with the α-XCENP-$E_{TAIL}$ immunoprecipitate. Immunoblotting of α-XCENP-$E_{TAIL}$ and α-XCENP-$E_{ROD}$ immunoprecipitates with α-XCENP-$E_{ROD}$ antibody revealed that one of the proteins is XCENP-E, and that the other protein of slightly lower molecular weight, is the additional XCENP-E related protein shown earlier to be recognized in inmanipulated extract by the α-XCENP-E$_{ROD}$ antibody. The presence of this XCENP-E-related protein in immunoprecipitates prepared using the α-XCENP-E$_{TAIL}$ antibody, which does not directly recognize this lower molecular weight species, provides evidence that like most kinesin-related proteins, XCENP-E exists in a complex that is at least dimeric.

Example V

Addition of α-XCENP-E Antibody Disrupts Metaphase Spindle Formation

As a further test of the requirement of CENP-E in mediating chromosome congression, especially in view of the removal of multiple proteins upon immunodepletion of XCENP-E, XCENP-E function was perturbed in situ by addition of the monospecific α-XCENP-E$_{TAIL}$ antibody to CSF-arrested Xenopus egg extracts. These extracts were cycled through interphase and arrested at the subsequent M-phase.

As observed upon immunodepletion of XCENP-E, addition of α-XCENP-E$_{TAIL}$ antibody resulted in almost total elimination of bipolar spindles with properly aligned chromosomes. This loss was accompanied by an increase in the percentage of bipolar spindles with misaligned chromosomes, indicating a role for XCENP-E in congression. Also observed was a large increase in the proportion of monopolar structures suggesting an additional role for XCENP-E in establishment or maintenance of spindle bipolarity. Similar results were obtained in four independent experiments, and also using α-XCENP-E$_{ROD}$ antibody.

The monopolar structures observed upon addition of α-XCENP-E antibody could arise from disruption of bipolar spindle assembly. This sort of spindle perturbation has also been observed following overexpression of the p50 subunit of dynactin, which also localizes to kinetochores (Echeverri, et al., *J. Cell Biol.* 132:617–633 (1996)). p50 overexpression disrupts spindle bipolarity, yielding two apparent monopoles. On the other hand, monopoles may also arise from disruption of sister chromatid cohesion upon entry into anaphase (Murray, et al., *Proc. Natl. Acad. Sci. USA* 93:12327–12332 (1996)). Since apparently non-disjoined sister chromatids are visible in structures formed in the presence of α-XCENP-E$_{TAIL}$ antibody, the monopolar structures observed for XCENP-E are unlikely to be the products of premature anaphase. These findings support a role for XCENP-E during prometaphase in establishment or maintenance of bipolarity, as well as in congression.

Consistent with an essential role for XCENP-E in chromosome movement, chromosomes associated with monopolar structures formed in the presence of anti-XCENP-E antibody were often found distributed both at the periphery and within the aster of microtubules. In contrast, the small proportion of monopolar structures formed in control extracts chromosomes were invariably localized at the periphery of the aster. Unlike perturbation of XKCM1, a relatively abundant Xenopus kinesin superfamily member, which induces formation of large asters as a consequence of decreased microtubule catastrophe (Walczak, et al., *Cell* 84:37–47 (1996)), the asters formed in extracts to which α-XCENP-E$_{TAIL}$ antibody was added, or from which XCENP-E had been removed, were not unusually large. This observation suggests that XCENP-E does not play a role in regulating microtubule dynamics analogous to that played by XKCM1.

What is claimed is:

1. An isolated nucleic acid sequence encoding a protein comprising an amino acid sequence that has greater than 80% amino acid sequence identity to amino acid residues 1–324 of SEQ ID NO:1, wherein said protein has at least one activity chosen from (a) plus end-directed microtubule motor activity, (b) ATPase activity, and (c) microtubule binding activity.

2. The isolated nucleic acid sequence of claim 1, wherein said sequence has a nucleotide sequence of SEQ ID NO:2.

3. The isolated nucleic acid sequence of claim 1, wherein said sequence encodes a protein having a molecular weight of about 300 to about 350 kDa.

4. The isolated nucleic acid sequence of claim 1, wherein said sequence encodes a protein having a plus-end directed core motor domain that has greater than 85% amino acid sequence identity to said Xenopus centromere-associated protein E core motor domain.

5. The isolated nucleic acid sequence of claim 1, wherein said sequence encodes a protein having a plus-end directed core motor domain that has greater than 90% amino acid sequence identity to said Xenopus centromere-associated protein E core motor domain.

6. The isolated nucleic acid sequence of claim 1, wherein said sequence encodes a protein having a plus-end directed core motor domain that has greater than 95% amino acid sequence identity to said Xenopus centromere-associated protein E core motor domain.

7. The isolated nucleic acid sequence of claim 1, wherein said protein has plus end-directed microtubule motor activity.

8. The isolated nucleic acid sequence of claim 1, wherein said protein has ATPase activity.

9. The isolated nucleic acid sequence of claim 1, wherein said protein has microtubule binding activity.

10. An isolated nucleic acid sequence encoding a protein comprising amino acid residues 1–324 of SEQ ID NO:1.

11. The isolated nucleic acid sequence of claim 10, wherein said protein has plus end-directed microtubule motor activity.

12. The isolated nucleic acid sequence of claim 10, wherein said protein has ATPase activity.

13. The isolated nucleic acid sequence of claim 10, wherein said protein has microtubule binding activity.

* * * * *